(12) United States Patent
Angibaud et al.

(10) Patent No.: US 7,129,356 B2
(45) Date of Patent: Oct. 31, 2006

(54) FARNESYL TRANSFERASE INHIBITING 4-SUBSTITUTED QUINOLINE AND QUINAZOLINE DERIVATIVES

(75) Inventors: Patrick René Angibaud, Fontaine-Bellenger (FR); Marc Gaston Venet, Le Mesnil-Esnard (FR)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 10/451,902

(22) PCT Filed: Dec. 21, 2001

(86) PCT No.: PCT/EP01/15234

§ 371 (c)(1), (2), (4) Date: Jun. 26, 2003

(87) PCT Pub. No.: WO02/051835

PCT Pub. Date: Jul. 4, 2002

(65) Prior Publication Data

US 2004/0063944 A1 Apr. 1, 2004

(30) Foreign Application Priority Data

Dec. 27, 2000 (EP) ................... 00204715

(51) Int. Cl.
C07D 215/16 (2006.01)
C07D 215/20 (2006.01)
C07D 401/02 (2006.01)
A61K 31/47 (2006.01)

(52) U.S. Cl. ............. 546/157; 546/156; 544/284; 514/311; 514/314; 514/315

(58) Field of Classification Search ............ 514/311, 514/314, 315; 546/157, 158; 544/284
See application file for complete search history.

(56) References Cited

U.S. PATENT DOCUMENTS 5,612,354 A * 3/1997 Sanz et al. ............ 514/314

FOREIGN PATENT DOCUMENTS

| EP | 0371564 B1 | 7/1995 |
| WO | WO 97/16443 * | 5/1997 |
| WO | WO 97/16443 A1 | 5/1997 |
| WO | WO 97/21701 * | 6/1997 |
| WO | WO 97/21701 A1 | 6/1997 |
| WO | WO 98/40383 A1 | 9/1998 |
| WO | WO 98/49157 * | 11/1998 |
| WO | WO 98/49157 A1 | 11/1998 |
| WO | WO 98/55124 A1 | 12/1998 |
| WO | WO 00/01386 A1 | 1/2000 |
| WO | WO 00/01411 A1 | 1/2000 |
| WO | WO 00/12498 * | 3/2000 |
| WO | WO 00/12498 A1 | 3/2000 |
| WO | WO 00/12499 * | 3/2000 |
| WO | WO 00/12499 A1 | 3/2000 |
| WO | WO 00/39082 A2 | 7/2000 |
| WO | WO 00/47574 A1 | 8/2000 |
| WO | WO 01/53289 A1 | 7/2001 |

OTHER PUBLICATIONS

Kohl et al., "Selective Inhibition of ras-Dependent Transformation by a Farnesyltransferase Inhibitor." *Science*, 1993, pp. 1934-1937, vol. 260, No. 5116.

Rak et al., "Mutant ras Oncogenes Upregulate VEGF/VPF Expression: Implications for Induction and Inhibition of Tumor Angiogenesis." *Cancer Research*, 1995, pp. 4575-4580, vol. 55, No. 20.

* cited by examiner

*Primary Examiner*—D. Margaret Seaman

(57) ABSTRACT

This invention comprises the novel compounds of formula (I)

wherein r, s, t, $Y^1$, $Y^2$, Z, $R^1$, $R^2$, $R^3$, $R^4$, $R^5$, $R^6$ and $R^7$ have defined meanings, having farnesyl transferase inhibiting activity; their preparation, compositions containing them and their use as a medicine.

15 Claims, No Drawings

FARNESYL TRANSFERASE INHIBITING 4-SUBSTITUTED QUINOLINE AND QUINAZOLINE DERIVATIVES

CROSS REFERENCE TO RELATED APPLICATIONS

This application is the national stage of Application No. PCT/EP01/15234, filed Dec. 21, 2001 which application claims priority from EP 00204715.7 filed Dec. 27, 2000.

FIELD OF THE INVENTION

The present invention is concerned with novel 4-substituted quinoline and quinazoline derivatives, the preparation thereof, pharmaceutical compositions comprising said novel compounds and the use of these compounds as a medicine as well as methods of treatment by administering said compounds.

BACKGROUND OF THE INVENTION

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumor cells. To acquire this transforming potential, the precursor of the $p21^{ras}$ oncoprotein must undergo an enzymatically catalyzed farnesylation of the cysteine residue located in a carboxyl-terminal tetrapeptide. Therefore, inhibitors of the enzymes that catalyzes this modification, i.e. farnesyl transferase, will prevent the membrane attachment of $p21^{ras}$ and block the aberrant growth of ras-transformed tumors. Hence, it is generally accepted in the art that farnesyl transferase inhibitors can be very useful as anticancer agents for tumors in which ras contributes to transformation.

Since mutated oncogenic forms of ras are frequently found in many human cancers, most notably in more than 50% of colon and pancreatic carcinomas (Kohl et al., Science, vol 260, 1834–1837, 1993), it has been suggested that farnesyl tranferase inhibitors can be very useful against these types of cancer.

In EP-0,371,564 there are described (1H-azol-1-ylmethyl) substituted quinoline and quinolinone derivatives which suppress the plasma elimination of retinoic acids. Some of these compounds also have the ability to inhibit the formation of androgens from progestines and/or inhibit the action of the aromatase enzyme complex.

In WO 97/16443, WO 97/21701, WO 98/40383 and WO 98/49157, there are described 2-quinolone derivatives which exhibit farnesyl transferase inhibiting activity. WO 00/39082 describes a class of novel 1,2-annelated quinoline compounds, bearing a nitrogen- or carbon-linked imidazole, which show farnesyl protein transferase and geranylgeranyl transferase inhibiting activity. Other quinolone compounds having farnesyl transferase inhibiting activity are described in WO 00/12498, 00/12499, 00/47574 and 01/53289.

Unexpectedly, it has been found that the present novel 4-substituted quinoline and quinazoline compounds show farnesyl protein transferase inhibiting activity.

DETAILED DESCRIPTION OF THE INVENTION

The present invention concerns compounds of formula (I):—

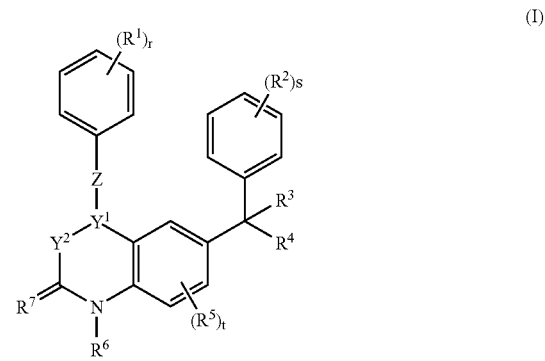

or a pharmaceutically acceptable salt or N-oxide or stereochemically isomeric form thereof, wherein
r and s are each independently 0, 1, 2, 3, 4 or 5;
t is 0, 1, 2 or 3;
$>Y^1—Y^2$— is a trivalent radical of formula

 (y-1)

 (y-2)

 (y-3)

 (y-4)

wherein $R^9$ is hydrogen, halo, cyano, $C_{1-6}$alkyl, hydroxy$C_{1-6}$alkyl, $C_{1-6}$alkyloxy$C_{1-6}$alkyl, —$(CR^{20}R^{21})_p$— —$C_{3-10}$cycloalkyl, $C_{2-6}$alkenyl, $C_{2-6}$alkynyl, halocarbonyl, hydroxycarbonyl, $C_{1-6}$alkyloxycarbonyl, aryl or a group of formula —$C_{1-6}$alkyl-$NR^{22}R^{23}$, —$C_{2-6}$alkenyl-$NR^{22}R^{23}$, —$CONR^{22}R^{23}$ or —$NR^{22}$—$C_{1-6}$alkyl-$NR^{22}R^{23}$;

Z is —O—, —S—, —SO—, —SO$_2$—, —$NR^{22}$—, -Alk-, $C_{2-4}$alkenediyl, —O-Alk-, -Alk-O—, —$S(O)_{0-2}$-Alk-, -Alk-$S(O)_{0-2}$, —OC(O)-Alk-, -Alk-OC(O)—, —$NR^{22}$-Alk-, -Alk-$NR^{22}$—, —$NR^{22}$—C(O)— or —C(O)—$NR^{22}$— (in which Alk is $C_{1-6}$alkanediyl) and in which the Alk or alkenediyl moiety may be optionally substituted by one or more substituents independently selected from $C_{1-6}$alkyl, $C_{1-6}$alkyloxy, aryl$C_{1-6}$alkyl or $Ar^2$, and where necessary to establish the configuration of any Z group, the first atom recited above in any such group being that which is linked to the $Y^1$ grouping in formula (I);

each $R^1$ and $R^2$ is independently azido, hydroxy, halo, cyano, nitro, $C_{1-6}$alkyl, —$(CR^{20}R^{21})_p$—$C_{3-10}$cycloalkyl, cyano$C_{1-6}$alkyl, hydroxy$C_{1-6}$alkyl, $C_{1-6}$alkyloxy$C_{1-6}$alkyl, hydroxycarbonyl$C_{1-6}$alkyloxy$C_{1-6}$alkyl, $R^{24}S$ $C_{1-6}$alkyl, trihalomethyl, aryl$C_{1-6}$alkyl, $Het^2C_{1-6}$alkyl, —$C_{1-6}$alkyl-$NR^{22}R^{23}$, —$C_{1-6}$alkyl$NR^{22}C_{1-6}$alkyl-$NR^{22}R^{23}$, —$C_{1-6}$alkyl$NR^{22}$-$Het^2$, —$C_{1-6}$alkyl$NR^{22}$—

$C_{1-6}$ alkyloxy$C_{1-6}$alkyl, —$C_{1-6}$alkylNR$^{22}$—$C_{1-6}$alkyl-S—$C_{1-6}$ alkyl-Ar$^2$, —$C_{1-6}$alkylNR$^{22}$—$C_{1-6}$alkyl-S—$C_{1-6}$ alkyl, —$C_{1-6}$alkylNR$^{22}C_{1-6}$alkyl-Ar$^2$ (in which the $C_{1-6}$alkyl moiety adjacent to the Ar$^2$ is optionally substituted by $C_{1-6}$alkyloxycarbonyl), —$C_{1-6}$alkylNR$^{22}C_{1-6}$ alkyl-Het$^2$, —$C_{1-6}$alkylNR$^{22}$COC$_{1-6}$alkyl, —$C_{1-6}$ alkylNR$^{22}$COAlkAr$^2$, —$C_{1-6}$alkylNR$^{22}$COAr$^2$, $C_{1-6}$alkylsulphonylamino$C_{1-6}$alkyl, $C_{1-6}$alkyloxy, hydroxy$C_{1-6}$alkyloxy, $C_{1-6}$alkyloxy$C_{1-6}$alkyloxy, —O$C_{1-6}$ alkyl-NR$^{22}$R$^{23}$, trihalomethoxy, aryl$C_{1-6}$alkyloxy, Het$^2C_{1-6}$alkyloxy, $C_{1-6}$alkylthio, $C_{2-6}$alkenyl, cyano$C_{2-6}$ alkenyl, —$C_{2-6}$alkenyl-NR$^{22}$R$^{23}$, hydroxycarbonyl$C_{2-6}$ alkenyl, $C_{1-6}$alkyloxycarbonyl$C_{2-6}$alkenyl, $C_{2-6}$alkynyl, —CHO, $C_{1-6}$alkylcarbonyl, hydroxy$C_{1-6}$ alkylcarbonyl, hydroxycarbonyl, $C_{1-6}$alkyloxycarbonyl, —CONR$^{22}$R$^{23}$, —CONR$^{22}$—$C_{1-6}$alkyl-NR$^{22}$R$^{23}$, —CONR$^{22}$—$C_{1-6}$ alkyl-Het$^2$, —CONR$^{22}$—$C_{1-6}$alkyl-Ar$^2$, —CONR$^{22}$-Het$^2$, —CONR$^{22}$Ar$^2$, —CONR$^{22}$—O—$C_{1-6}$alkyl, —CONR$^{22}$—$C_{1-6}$alkenyl, —NR$^{22}$R$^{23}$, —OC(O)R$^{24}$, —CR$^{24}$=NR$^{25}$, —CR$^{24}$=N—OR$^{25}$, —NR$^{24}$C(O) NR$^{22}$R$^{23}$, —NR$^{24}$SO$_2$R$^{25}$, —NR$^{24}$C(O)R$^{25}$, —S(O)$_{0-2}$ R$^{24}$, —SO$_2$NR$^{24}$R$^{25}$, —C(NR$^{26}$R$^{27}$)=NR$^{28}$; —Sn(R$^{24}$)$_3$, —SiR$^{24}$R$^{24}$R$^{25}$, —B(OR$^{24}$)$_2$, —P(O)OR$^{24}$OR$^{25}$, Ar$^2$oxy, Het$^2$-oxy, or a group of formula -Z, —CO-Z or —CO—NR$^y$-Z in which R$^y$ is hydrogen or $C_{1-4}$alkyl and Z is phenyl or a 5- or 6-membered heterocyclic ring containing one or more heteroatoms selected from oxygen, sulphur and nitrogen, the phenyl or heterocyclic ring being optionally substituted by one or two substituents each independently selected from halo, cyano, —COOR$^{24}$, aminocarbonyl, $C_{1-6}$alkylthio, hydroxy, —NR$^{22}$R$^{23}$, $C_{1-6}$alkylsulphonylamino, $C_{1-6}$alkyl, halo$C_{1-6}$alkyl, $C_{1-6}$alkyloxy or phenyl; or two R$^1$ or R$^2$ substituents adjacent to one another on the phenyl ring may form together a bivalent radical of formula —O—CH$_2$—O— (a-1)

—O—CH$_2$—CH$_2$—O— (a-2)

—O—CH=CH— (a-3)

—O—CH$_2$—CH$_2$— (a-4)

—O—CH$_2$—CH$_2$—CH$_2$— (a-5)

—CH=CH—CH=CH— (a-6)

p is 0 to 5;

R$^{20}$ and R$^{21}$ are independently hydrogen or $C_{1-6}$ alkyl and are independently defined for each iteration of p in excess of 1;

R$^{22}$ and R$^{23}$ are independently hydrogen, $C_{1-6}$ alkyl or —(CR$^{20}$R$^{21}$)$_p$ —$C_{3-10}$cycloalkyl, or together with the adjacent nitrogen atom form a 5- or 6-membered heterocyclic ring optionally containing one, two or three further heteroatoms selected from oxygen, nitrogen or sulphur and optionally substituted by one or two substituents each independently selected from halo, hydroxy, cyano, nitro, $C_{1-6}$alkyl, halo$C_{1-6}$alkyl, $C_{1-6}$alkyloxy, OCF$_3$, hydroxycarbonyl, $C_{1-6}$alkyloxycarbonyl, aminocarbonyl, mono- or di-($C_{1-6}$alkyl)aminocarbonyl, amino, mono- or di-($C_{1-6}$alkyl)amino, $C_{1-6}$alkylsulfonylamino, oxime, or phenyl;

R$^{24}$ and R$^{25}$ are independently hydrogen, $C_{1-6}$ alkyl, —CR$_{20}$R$_{21}$)p—$C_{3-10}$cycloalkyl or aryl$C_{1-6}$alkyl;

R$^{26}$, R$^{27}$ and R$^{28}$ are independently hydrogen and $C_{1-6}$alkyl or C(O) $C_{1-6}$alkyl;

R$^3$ is hydrogen, halo, cyano, $C_{1-6}$alkyl, —(CR$^{20}$R$^{21}$)$_p$ —$C_{3-10}$cycloalkyl, halo$C_{1-6}$alkyl, cyano$C_{1-6}$alkyl, hydroxy$C_{1-6}$alkyl, $C_{1-6}$alkyloxy$C_{1-6}$alkyl, aryl$C_{1-6}$alkyloxy$C_{1-6}$alkyl, $C_{1-6}$alkylthio$C_{1-6}$alkyl, hydroxycarbonyl$C_{1-6}$alkyl, $C_{1-6}$alkylcarbonyl$C_{1-6}$alkyl, $C_{1-6}$alkyloxycarbonyl$C_{1-6}$alkyl, —$C_{1-6}$alkyl-NR$^{22}$R$^{23}$, —$C_{1-6}$alkyl-CONR$^{22}$R$^{23}$, aryl$C_{1-6}$alkyl, Het$^2C_{1-6}$alkyl, $C_{2-6}$alkenyl, —$C_{2-6}$alkenyl NR$^{22}$R$^{23}$, $C_{2-6}$alkynyl, hydroxycarbonyl, $C_{1-6}$alkyloxycarbonyl, aryl, or Het$^2$; or a radical of formula —O—R$^{10}$ (b-1)

—S—R$^{10}$ (b-2)

—NR$^{11}$R$^{12}$ (b-3)

—N=CR$^{10}$R$^{11}$ (b-4)

wherein R$^{10}$ is hydrogen, $C_{1-6}$alkyl, —(CR$^{20}$R$^{21}$)$_p$ —$C_{3-10}$cycloalkyl, aryl$C_{1-6}$alkyl, $C_{2-6}$alkenyl, $C_{2-6}$alkynyl, $C_{1-6}$alkylcarbonyl, aryl, a group of formula —NR$^{22}$R$^{23}$ or —$C_{1-6}$alkylC(O)OC$_{1-6}$alkyl NR$^{22}$R$^{23}$, or a radical of formula -Alk-OR$^{13}$ or -Alk-NR$^{14}$R$^{15}$;

R$^{11}$ is hydrogen, $C_{1-6}$alkyl, —(CR$^{20}$R$^{21}$)$_p$—$C_{3-10}$cycloalkyl, $C_{2-6}$alkenyl, $C_{2-6}$alkynyl, aryl or aryl$C_{1-6}$alkyl;

R$^{12}$ is hydrogen, hydroxy, $C_{1-6}$alkyl, —(CR$^{20}$R$^{21}$)$_p$ —$C_{3-10}$cycloalkyl, $C_{1-6}$alkylcarbonyl$C_{1-6}$alkyl, aryl$C_{1-6}$alkyl, $C_{2-6}$alkenyl, $C_{2-6}$alkynyl, aryl, $C_{1-6}$alkyloxy, a group of formula —NR$^{22}$R$^{23}$, $C_{1-6}$alkylcarbonylamino, $C_{1-6}$alkylcarbonyl, halo$C_{1-6}$ alkylcarbonyl, aryl$C_{1-6}$alkylcarbonyl, Het$^2C_{1-6}$ alkylcarbonyl, arylcarbonyl, $C_{1-6}$alkyloxycarbonyl, trihalo$C_{1-6}$alkyloxycarbonyl, $C_{1-6}$alkyloxy$C_{1-6}$alkylcarbonyl, aminocarbonyl, mono- or di-($C_{1-6}$alkyl)aminocarbonyl wherein the alkyl moiety may optionally be substituted by one or more substituents independently selected from aryl and $C_{1-6}$alkyloxycarbonyl substituents; aminocarbonylcarbonyl, mono- or di-($C_{1-6}$alkyl)amino$C_{1-6}$alkylcarbonyl, or a radical of formula -Alk-OR$^{13}$ or -Alk-NR$^{14}$R$^{15}$;

R$^{13}$ is hydrogen, $C_{1-6}$alkyl, —(CR$^{20}$R$^{21}$)$_p$—$C_{3-10}$cycloalkyl, $C_{2-6}$alkenyl, $C_{2-6}$alkynyl, $C_{1-6}$alkylcarbonyl, hydroxy$C_{1-6}$alkyl, aryl or aryl$C_{1-6}$alkyl;

R$^{14}$ is hydrogen, $C_{1-6}$alkyl, —(CR$^{20}$R$^{21}$)$_p$ —$C_{3-10}$cycloalkyl, $C_{2-6}$alkenyl, $C_{2-6}$alkynyl, aryl or aryl$C_{1-6}$ alkyl;

R$^{15}$ is hydrogen, $C_{1-6}$alkyl, —(CR$^{20}$R$^{21}$)$_p$—$C_{3-10}$cycloalkyl, $C_{2-6}$alkenyl, $C_{2-6}$alkynyl, $C_{1-6}$alkylcarbonyl, aryl or aryl$C_{1-6}$alkyl;

R$^4$ is a radical of formula

 (c-1)

or

-continued (c-2)

[structure with N ring, R16, R17]

or (c-3)

[structure with N-N ring, R18, R18a]

or (c-4)

[pyridine-like structure with R16]

wherein $R^{16}$ is hydrogen, halo, $C_{1-6}$alkyl, $—(CR^{20}R^{21})_p$ $—C_{3-10}$cycloalkyl, hydroxy$C_{1-6}$alkyl, $C_{1-6}$alkyloxy$C_{1-6}$ alkyl, $C_{1-6}$alkylS(O)$_{0-2}C_{1-6}$alkyl, $C_{1-6}$alkyloxy, $C_{1-6}$alkylthio, a group of formula $—NR^{22}R^{23}$, $—NHCOC_{1-6}$alkyl, hydroxycarbonyl, $C_{1-6}$alkyloxycarbonyl or aryl, $R^{17}$ is hydrogen, $C_{1-6}$alkyl, $—(CR^{20}R^{21})_p$ $—C_{3-10}$cycloalkyl, hydroxy$C_{1-6}$alkyl, $C_{1-6}$alkyloxy$C_{1-6}$alkyl, aryl $C_{1-6}$alkyl, trifluoromethyl, trifluoromethyl$C_{1-6}$ alkyl, hydroxycarbonyl$C_{1-6}$alkyl, $C_{1-6}$alkyloxycarbonyl$C_{1-6}$alkyl, mono- or di-($C_{1-6}$alkyl)aminosulphonyl or $—C_{1-6}$alkyl P(O)OR$^{24}$OR$^{25}$;

$R^{18}$ is hydrogen, $C_{1-6}$alkyl, $—(CR^{20}R^{21})_p$ $—C_{3-10}$cycloalkyl, aryl$C_{1-6}$alkyl or $C_{1-6}$alkyloxy$C_{1-6}$alkyl;

$R^{18a}$ is hydrogen, $—SH$ or $—SC_{1-4}$alkyl;

$R^5$ is cyano, hydroxy, halo, $C_{1-6}$alkyl, $—(CR^{20}R^{21})_p$ $—C_{3-10}$ cycloalkyl, $C_{2-6}$alkenyl, $C_{2-6}$alkynyl, $C_{1-6}$alkyloxy, aryl$C_{1-6}$alkyloxy, Het$^2C_{1-6}$alkyloxy, hydroxycarbonyl, $C_{1-6}$alkyloxycarbonyl, or a group of formula $—NR^{22}R^{23}$ or $—CONR^{22}R^{23}$;

$R^6$ is hydrogen, $C_{1-6}$alkyl, $—(CR^{20}R^{21})_p$ $—C_{3-10}$cycloalkyl, cyano$C_{1-6}$alkyl, $—C_{1-6}$alkylCO$_2R^{24}$, aminocarbonyl$C_{1-6}$ alkyl or $—C_{1-6}$alkyl-NR$^{22}R^{23}$, R$^{24}$SO$_2$, R$^{24}$SO$_2C_{1-6}$ alkyl, $—C_{1-6}$alkyl-OR$^{24}$, $—C_{1-6}$alkyl-SR$^{24}$, $—C_{1-6}$alkyl-CONR$^{22}$—$C_{1-6}$alkyl-NR$^{22}R^{23}$, $—C_{1-6}$alkylCONR$^{22}$—$C_{1-6}$alkyl-Het$^2$, $—C_{1-6}$alkyl CONR$^{22}$—$C_{1-6}$alkyl-Ar$^2$, $—C_{1-6}$alkyl CONR$^{22}$-Het$^2$, $—C_{1-6}$alkyl CONR$^{22}$Ar$^2$, $—C_{1-6}$alkyl CONR$^{22}$—O—$C_{1-6}$alkyl, $—C_{1-6}$alkyl CONR$^{22}$—$C_{1-6}$alkenyl, -Alk-Ar$^2$ or -Alk-Het$^2$;

$R^7$ is oxygen or sulphur; or $R^6$ and $R^7$ together form a trivalent radical of formula:—

| | | | |
|---|---|---|---|
| $—CR^{30}$=$CR^{31}$—N= | (x-1) | $—CR^{30}$=$CR^{31}$—$CR^{32}$= | (x-6) |
| $—CR^{30}$=N—N= | (x-2) | $—CR^{30}$=N—$CR^{31}$= | (x-7) |
| $—C(=O)$—NH—N= | (x-3) | $—C(=O)$—NH—$CR^{30}$= | (x-8) |
| $—N$=N—N= | (x-4) | $—N$=N—$CR^{30}$= | (x-9) or |
| $—N$=$CR^{30}$—N= | (x-5) | $—CH_2$—$(CH_2)_{0-1}$—$CH_2$—N= | (x-10) | wherein each $R^{30}$, $R^{31}$ and $R^{32}$ are independently hydrogen, $C_{1-6}$ alkyl, $—OR^{24}$, $—COOR^{24}$, $—NR^{22}R^{23}$, $—C_{1-6}$alkylOR$^{24}$, $—C_{1-6}$alkylSR$^{24}$, R$^{23}$R$^{22}$NC$_{1-6}$ alkyl-, $—CONR^{22}R^{23}$, $C_{2-6}$alkenyl, $C_{2-6}$alkenylAr$^2$, $C_{2-6}$alkenylHet$^2$, cyano, amino, thio, $C_{1-6}$ alkylthio, $—O$-Ar$^2$, $—S$-Ar$^2$ or Ar$^2$;

Ar$^2$ is phenyl, naphthyl or phenyl or naphthyl substituted by one to five substituents each independently selected from halo, hydroxy, cyano, nitro, $C_{1-6}$alkyl, haloC$_{1-6}$ alkyl, -alkylNR$^{22}R^{23}$, $C_{1-6}$alkyloxy, OCF$_3$, hydroxycarbonyl, $C_{1-6}$alkyloxycarbonyl, aryloxy, $—NR^{22}R^{23}$, $C_{1-6}$alkylsulfonylamino, oxime or phenyl, or a bivalent substituent of formula $—O—CH_2—O—$ or $—O—CH_2—CH_2—O—$;

Het$^2$ is a mono- or bi-cyclic heterocyclic ring containing one or more heteroatoms selected from oxygen, sulphur and nitrogen and optionally substituted by one or two substituents each independently selected from halo, hydroxy, cyano, nitro, $C_{1-6}$alkyl, haloC$_{1-6}$alkyl, -alkylNR$^{22}R^{23}$, $C_{1-6}$alkyloxy, OCF$_3$, hydroxycarbonyl, $C_{1-6}$alkyloxycarbonyl, $—CONR^{22}R^{23}$, $—NR^{22}R^{23}$, $C_{1-6}$alkylsulfonylamino, oxime or phenyl.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, e.g. methyl, ethyl, propyl, butyl, 1-methylethyl, 2-methylpropyl and the like; $C_{1-6}$alkyl includes $C_{1-4}$alkyl and the higher homologues thereof having 5 to 6 carbon atoms such as, for example, pentyl, 2-methyl-butyl, hexyl, 2-methylpentyl and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; haloC$_{1-6}$alkyl defines $C_{1-6}$alkyl containing one or more halo substituents for example trifluoromethyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like. The term "S(O)" refers to a sulfoxide and "S(O)$_2$" to a sulfone. Aryl defines phenyl, naphthalenyl or phenyl substituted with one or more substituents each independently selected from halo, $C_{1-6}$alkyl, $C_{1-6}$alkyloxy or trifluoromethyl, cyano, hydroxycarbonyl.

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fuimaric, malic, tartaric, citric, methanesulfonic, ethanesulfonic, benzenesulfonic, p-toluenesulfonic, cyclamic, salicylic, p-amino-salicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable acid addition salts and all stereoisomeric forms.

Examples of compounds of formula (I) include those wherein one or more of the following restrictions apply:

r and s are each independently 0, 1 or 2;

t is 0 or 1;

$>Y^1-Y^2-$ is a trivalent radical of formula $$>C=N- \qquad (y\text{-}1)$$

$$>C=CR^9- \qquad (y\text{-}2)$$

wherein $R^9$ is hydrogen, cyano, halo, $C_{1-6}$alkyl, hydroxy$C_{1-6}$alkyl, hydroxycarbonyl or aminocarbonyl;

Z is $C_{1-2}$ alkanediyl;

$R^1$ is halo, $C_{1-6}$alkyl, $-(CR^{20}R^{21})_p-C_{3-10}$cycloalkyl, trihalomethyl, trihalomethoxy, $C_{2-6}$alkenyl, hydroxycarbonyl$C_{2-6}$alkenyl, $C_{2-6}$alkynyl, $C_{1-6}$alkyloxy, hydroxy$C_{1-6}$alkyloxy, amino$C_{1-6}$alkyloxy, $C_{1-6}$alkylthio, hydroxycarbonyl, $C_{1-6}$alkyloxycarbonyl, $-CONR^{22}R^{23}$ or $-CH=NOR^{25}$; or two $R^1$ substituents adjacent to one another on the phenyl ring may independently form together a bivalent radical of formula $$-O-CH_2-O- \qquad (a\text{-}1)$$

$$-O-CH_2-CH_2-O- \qquad (a\text{-}2)$$

$R^2$ is halo, cyano, nitro, $C_{1-6}$alkyl, cyano$C_{1-6}$alkyl, $-C_{1-6}$alkyl $NR^{22}R^{23}$; cyano$C_{2-6}$alkenyl, $-NR^{22}R^{23}$, $-CHO$, $-CR^{24}=N-OR^{25}$, $C_{1-6}$alkyloxycarbonyl, $-CO\ NR^{22}R^{23}$; or two $R^2$ substituents adjacent to one another on the phenyl ring may independently form together a bivalent radical of formula $$-O-CH_2-O- \qquad (a\text{-}1)$$

$$-O-CH_2-CH_2-O- \qquad (a\text{-}2)$$

$R^3$ is hydrogen, $C_{1-6}$alkyl, $-(CR^{20}R^{21})_p-C_{3-10}$cycloalkyl, halo$C_{1-6}$alkyl, cyano$C_{1-6}$alkyl, hydroxy$C_{1-6}$alkyl, $C_{1-6}$alkyloxy$C_{1-6}$alkyl, $-C_{1-6}$alkyl $NR^{22}R^{23}$, Het$^2C_{1-6}$alkyl, $-C_{2-6}$alkenyl $NR^{22}R^{23}$, or -Het$^2$; or a group of formula $$-O-R^{10} \qquad (b\text{-}1)$$

$$-NR^{11}R^{12} \qquad (b\text{-}3)$$

wherein $R^{10}$ is hydrogen, $C_{1-6}$alkyl, or $-(CR^{20}R^{21})_p-C_{3-10}$cycloalkyl, or a group of formula -Alk-OR$^{13}$ or -Alk-NR$^{14}$R$^{15}$;

$R^{11}$ is hydrogen or $C_{1-6}$alkyl;

$R^{12}$ is hydrogen, hydroxy, $C_{1-6}$alkyl, $-(CR^{20}R^{21})_p-C_{3-10}$cycloalkyl, $C_{1-6}$alkyloxy, $C_{1-6}$alkylcarbonyl, arylC$_{1-6}$alkylcarbonyl, Het$^2$C$_{1-6}$alkylcarbonyl, aminocarbonyl, or a radical of formula -Alk-OR$^{13}$ or Alk-NR$^{14}$R$^{15}$;

wherein Alk is $C_{1-6}$alkanediyl;

$R^{13}$ is hydrogen, $C_{1-6}$alkyl or $-(CR^{20}R^{21})_p-C_{3-10}$cycloalkyl;

$R^{14}$ is hydrogen, $C_{1-6}$alkyl, or $-(CR^{20}R^{21})_p-C_{3-10}$cycloalkyl;

$R^{15}$ is hydrogen or $C_{1-6}$alkyl;

$R^4$ is a radical of formula (c-2) or (c-3)

wherein $R^{16}$ is hydrogen, halo or $C_{1-6}$alkyl, $R^{17}$ is hydrogen, $C_{1-6}$alkyl, $-(CR^{20}R^{21})_p-C_{3-10}$cycloalkyl, $C_{1-6}$alkyloxy$C_{1-6}$alkyl or trifluoromethyl;

$R^{18}$ is hydrogen, $C_{1-6}$alkyl or $-(CR^{20}R^{21})_p-C_{3-10}$cycloalkyl;

$R^{18a}$ is hydrogen:

$R^5$ is cyano, halo, $C_{1-6}$alkyl, $C_{2-6}$alkynyl, $C_{1-6}$alkyloxy or $C_{1-6}$alkyloxycarbonyl:

$R^6$ is hydrogen, $C_{1-6}$alkyl, $-C_{1-6}$alcylCO$_2$R$^{24}$, $-C_{1-6}$alkylC(O)NR$^{22}$R$^{23}$, -Alk-Ar$^2$, -AlkHet$^2$ or $-(CR^{20}R^{21})_p-C_{3-10}$cycloalkyl, $R^7$ is oxygen or sulphur; or $R^6$ and $R^7$ together form a trivalent radical of formula (x-1), (x-2), (x-3), (x-4) or (x-9)

Het$^2$ is a 5- or 6-membered monocyclic heterocyclic ring containing one, two or three heteroatoms selected from oxygen, sulphur or nitrogen for example pyrrolidinyl, imidazolyl, triazolyl, pyridyl, pyrimidinyl, furyl, morpholinyl, piperazinyl, piperidinyl, thiophenyl, thiazolyl or oxazolyl, or a 9- or 10-membered bicyclic heterocyclic ring especially one in which a benzene ring is fused to a heterocyclic ring containing one, two or three heteroatoms selected from oxygen, sulphur or nitrogen for example indolyl, quinolinyl, benzimidazolyl, benzotriazolyl, benzoxazolyl, benzothiazolyl or benzodioxolanyl.

A group of interesting compounds consists of those compounds of formula (I) wherein one or more of the following restrictions apply:

r is 0, 1 or 2;

s is 0 or 1;

t is 0;

$>Y^1-Y^2-$ is a trivalent radical of formula (y-1) or (y-2), wherein $R^9$ is hydrogen or halo;

Z is $C_{1-2}$ alkanediyl;

$R^1$ is halo, $C_{1-6}$alkyl, $C_{2-6}$alkenyl, $C_{2-6}$alkynyl or two $R^1$ substituents ortho to one another on the phenyl ring may independently form together a bivalent radical of formula (a-1);

$R^2$ is halo, cyano, nitro, CHO, $-CR^{24}=N-OR^{25}$ in which $R^{24}$ is hydrogen and $R^{25}$ is hydrogen or $C_{1-6}$alkyl, or two $R^2$ substituents ortho to one another on the phenyl ring may independently form together a bivalent radical of formula (a-1);

$R^3$ is hydrogen or a group of formula (b-1) or (b-3) wherein $R^{10}$ is hydrogen or a group of formula -Alk-OR$^{13}$.

$R^{11}$ is hydrogen;

$R^{12}$ is hydrogen, $C_{1-6}$alkyl, $C_{1-6}$alkylcarbonyl, hydroxy or $C_{1-6}$alkyloxy;

Alk is $C_{1-6}$alkanediyl and $R^{13}$ is hydrogen;

$R^4$ is a group of formula (c-2) or (c-3) wherein $R^{16}$ is hydrogen, halo or $C_{1-6}$alkyl;

$R^{17}$ is hydrogen or $C_{1-6}$alkyl;

$R^{18}$ is hydrogen or $C_{1-6}$alkyl;

$R^{18a}$ is hydrogen;

R⁶ is hydrogen, —(CR²⁰R²¹)$_p$—C$_{3-10}$cycloalkyl, —C$_{1-6}$alkylCO$_2$R²⁴, —C$_{1-6}$alkylC(O)NR²²R²³, -Alk-Ar² or -AlkHet² or C$_{1-6}$alkyl;

R⁷ is oxygen or sulphur; or R⁶ and R⁷ together form a trivalent radical of formula (x-1), (x-2), (x-3), (x-4) or (x-9)

aryl is phenyl.

A particular group of compounds consists of those compounds of formula (I) wherein r is 0 or 1, s is 1, t is 0, >Y¹—Y² is a trivalent radical of formula (y-1) or (y-2), Z is C$_{1-2}$ alkanediyl R¹ is halo, C$_{1-6}$alkyl or forms a bivalent radical of formula (a-1), R² is halo or cyano, R³ is hydrogen or a radical of formula (b-1) or (b-3) wherein R¹⁰ is hydrogen or -Alk-OR¹³, R¹¹ is hydrogen, R¹² is hydrogen or C$_{1-6}$alkylcarbonyl and R¹³ is hydrogen; R⁴ is a radical of formula (c-2) or (c-3) wherein R¹⁶ is hydrogen, R¹⁷ is C$_{1-6}$alkyl, R¹⁸ is C$_{1-6}$alkyl and R¹⁸ᵃ is hydrogen;

R⁶ is hydrogen, C$_{1-6}$alkyl, —CH$_2$—C$_{3-10}$cycloalkyl, —C$_{1-6}$alkylCO$_2$R²⁴ (R²⁴=H,Et), aminocarbonylC$_{1-6}$alkyl, -Alk-Ar² or -AlkHet²;

R⁷ is oxygen or sulphur; or R⁶ and R⁷ together form a trivalent radical of formula (x-2), (x-3) or (x-4).

More preferred compounds are those compounds of formula (I) wherein r is 0 or 1, s is 1, t is 0, >Y¹—Y² is a trivalent radical of formula (y-1) or (y-2), Z is C$_{1-2}$ alkanediyl, R¹ is halo, preferably chloro and most preferably 3-chloro, R² is halo, preferably 4-chloro or 4-fluoro, or cyano, preferably 4-cyano, R³ is hydrogen or a radical of formula (b-1) or (b-3), R⁹ is hydrogen, R¹⁰ is hydrogen, R¹¹ is hydrogen and R¹² is hydrogen or C$_{1-6}$alkylcarbonyl, R⁴ is a radical of formula (c-2) or (c-3) wherein R¹⁶ is hydrogen, R¹⁷ is C$_{1-6}$alkyl, R¹⁸ is C$_{1-6}$alkyl and R¹⁸ᵃ is hydrogen;

R⁶ is hydrogen, C$_{1-6}$alkyl, —CH$_2$—C$_{3-10}$cycloalkyl or —C$_{1-6}$alkylAr²;

R⁷ is oxygen or sulphur; or R⁶ and R⁷ together form a trivalent radical of formula (x-2) or (x-4).

Especially preferred compounds are those compounds of formula (I) wherein r and s are 1, t is 0, >Y¹—Y² is a trivalent radical of formula (y-1) or (y-2), Z is —(CH$_2$)$_2$—, R¹ is halo, preferably chloro, and most preferably 3-chloro, R² is halo, preferably chloro, and most preferably 4-chloro, or cyano, preferably 4-cyano, R³ is a radical of formula (b-1) or (b-3) wherein R⁹ is hydrogen, R¹⁰ and R¹¹ are hydrogen and R¹² is hydrogen or C$_{1-6}$alkylcarbonyl; R⁴ is a radical of formula (c-2) or (c-3) wherein R¹⁶ is hydrogen, R¹⁷ is C$_{1-6}$alkyl preferably methyl, R¹⁸ is C$_{1-6}$alkyl preferably methyl and R¹⁸ᵃ is hydrogen; R⁶ is hydrogen, C$_{1-6}$alkyl, —CH$_2$—C$_{3-10}$cycloalkyl or —C$_{1-6}$alkylAr²; R⁷ is oxygen or sulphur; or R⁶ and R⁷ together form a trivalent radical of formula (x-4).

The most preferred compounds according to the invention are:—

6-[amino(4-chlorophenyl)(1-methyl-1H-imidazol-5-yl)methyl]-4-[2-(3-chlorophenyl)ethyl]-1-methyl-2(1H)-quinolinone 4-[2-(3-chlorophenyl)ethyl]-6-[(4-chlorophenyl)hydroxy(1-methyl-1H-imidazol-5-yl)methyl]-1-methyl-2(1H)-quinolinone α-(4-chlorophenyl)-5-[2-(3-chlorophenyl)ethyl]-α-(1-methyl-1H-imidazol-5-yl)-tetrazolo[1,5-α]quinoline-7-methanamine N-[(4-chlorophenyl)[5-[2-(3-chlorophenyl)ethyl]tetrazolo[1,5-α]quinolin-7-yl](1-methyl-1H-imidazol-5-yl)methyl]-acetamide N-[(4-chlorophenyl)(1-methyl-1H-imidazol-5-yl)[5-(2-phenylethyl)tetrazolo[1,5-α]quinolin-7-yl]methyl]-acetamide and 4-[2-(3-chlorophenyl)ethyl]-6-[(4-chlorophenyl)hydroxy(4-methyl-4H-1,2,4-triazol-3-yl)methyl]-1-methyl-2(1H)-quinolinone and their pharmaceutically acceptable salts.

The compounds of formula (I) and their pharmaceutically acceptable salts and N-oxides and stereochemically isomeric forms thereof may be prepared in conventional manner, for example by a process which comprises:— a) cyclising a compound of formula (II):

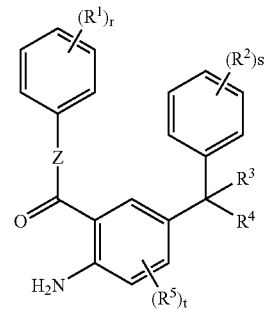

(II)

with a reagent serving to form a compound of formula (I) in which R⁶ is hydrogen and R⁷ is oxygen;

b) reacting a compound of formula (III):

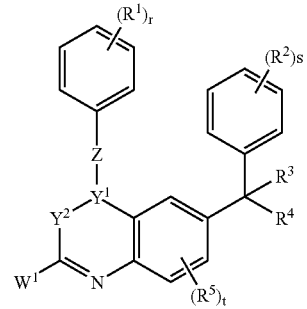

(III)

in which W¹ represents a replaceable or reactive group, with a reagent serving either to react with or replace the W¹ group in compound (III) to form a compound of formula (I) in which R⁶ is hydrogen and R⁷ is an oxygen or sulphur group or to react with the W¹ group and the adjacent nitrogen atom to form directly or indirectly a compound of formula (I) in which R⁶ and R⁷ together form a trivalent radical selected from formulae (x-1) to (x-10); or c) reacting a compound of formula (IV):

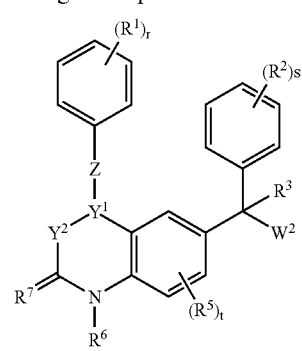

(IV)

in which W² is a replaceable group, with an imidazole reagent serving to replace the group W² with an R⁴ group of formula (c-1); or d) reacting a compound of formula (V):

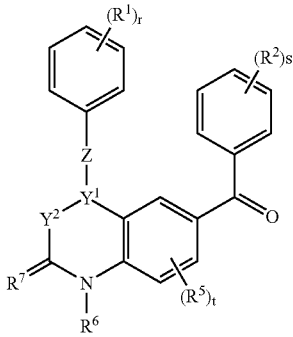

with an imidazole reagent to form a compound of formula (I) in which $R^4$ is a group of formula (c-2), or with a 3-mercapto-4-$C_{1-6}$alkyl-1,2,4-triazole reagent to form the corresponding 3-mercapto-4-$C_{1-6}$alkyl-1,2,4-triazole derivative, which is optionally methylated to form the corresponding 3-methylmercapto derivative, and subsequently removing the 3-mercapto or 3-methylmercapto group to form a compound of formula (I) in which $R^4$ is a group of formula (c-3) in which $R^{18}$ is a $C_{1-6}$alkyl group;

or with a 3-bromopyridyl reagent to form a compound of formula (I) wherein $R^4$ is a group of formula (c-4); or e) reacting a compound of formula (VI):

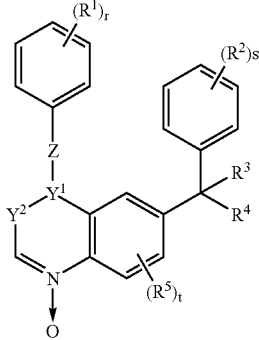

with a reagent serving to convert the said compound (VI) to a compound of formula (I) in which $R^6$ is hydrogen and $R^7$ is oxygen;

and optionally effecting one or more of the following conversions in any desired order:—
  (i) converting a compound of formula (I) into a different compound of formula (I);
  (ii) converting a compound of formula (I) in to a pharmaceutically acceptable salt or N-oxide thereof;
  (iii) converting a pharmaceutically acceptable salt or N-oxide of a compound of formula (I) into the parent compound of formula (I);
  (iv) preparing a stereochemical isomeric form of a compound of formula (I) or a pharmaceutically acceptable salt or N-oxide thereof.

With regard to process a), this can be effected as described for example in WO 97/21701 and WO98/49157 referred to above. Thus, the cyclisation may be effected for example by subjecting the compound of formula (II) to an acetylation reaction, e.g. by treatment with the anhydride of a carboxylic acid, e.g. acetic anhydride in a reaction-inert solvent, e.g. toluene, and subsequent reaction with a base such as potassium tert-butoxide in a reaction-inert solvent such as 1,2-dimethoxyethane.

With regard to process b), this can also be effected as described for example in WO 97/21701 and WO98/49157 referred to above for the preparation of compounds in which $R^7$ is oxygen, for example by hydrolysis of an ether of formula (II) in which W1 is $C_{1-6}$alkyloxy in an aqueous acid solution such hydrochloric acid With regard to process b), for the preparation of compounds in which $R^6$ and $R^7$ together form a trivalent radical of formula (x-1) to (x-10), this can be effected as described for example in WO 00/39082 referred to above. For example, when $W^1$ is chloro, the compound of formula (III) can be reacted with an azide compound for example sodium azide to form a corresponding compound of formula (I) in which $R^6$ and $R^7$ together form a trivalent radical of formula (x-4).

With regard to process c), this can be effected for example by N-alkylating an intermediate of formula (IV), wherein $W^2$ is an appropriate leaving group such as, for example, chloro, bromo, methanesulfonyloxy or benzenesulfonyloxy, with an intermediate of formula (IVa) to form a a compound of formula (I) in which $R^4$ is a group of formula (c-1) represented by compounds of formula (I-a):

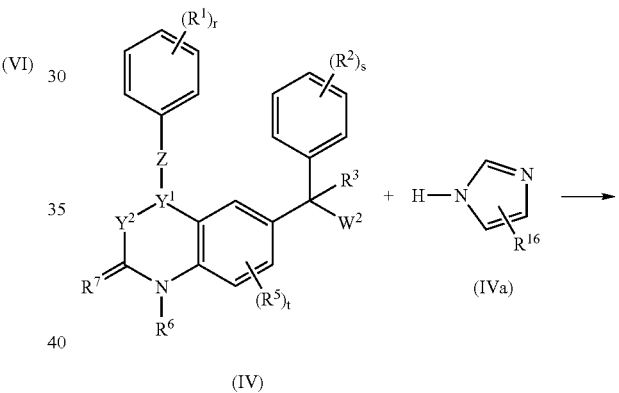

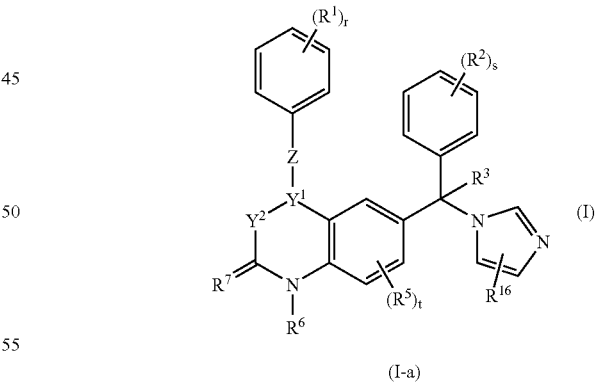

The reaction can be performed in a reaction-inert solvent such as, for example, acetonitrile, and optionally in the presence of a suitable base such as, for example, sodium carbonate, potassium carbonate or triethylamine. Stirring may enhance the rate of the reaction. The reaction may conveniently be carried out at a temperature ranging between room temperature and reflux temperature.

Also, compounds of formula (I-a) can be prepared by reacting an intermediate of formula (V) in which $W^2$ is hydroxy with an intermediate of formula (X), wherein Y is oxygen or sulfur, such as, for example, a 1,1'-carbonyldiimidazole.

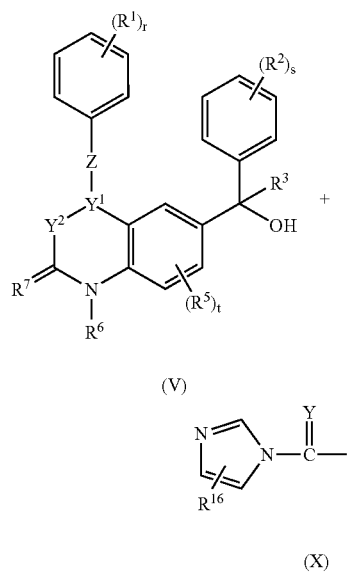

(V)

(X)

Said reaction may conveniently be conducted in a reaction-inert solvent, such as, e.g. tetrahydrofuran, optionally in the presence of a base, such as sodium hydride, and at a temperature ranging between room temperature and the reflux temperature of the reaction mixture.

With regard to process d), the compounds of formula (I) wherein $R^4$ represents a radical of formula (c-2), $R^3$ is hydroxy and $R^{17}$ is $C_{1-6}$alkyl, said compounds being referred to as compounds of formula (I-b-1) may be prepared by reacting an intermediate ketone of formula (V) with an intermediate of formula (III-1). Said reaction requires the presence of a suitable strong base, such as, for example, butyl lithium in an appropriate solvent, such as, for example, tetrahydrofuran, and the presence of an appropriate silane derivative, such as, for example, triethylchlorosilane. During the work-up procedure an intermediate silane derivative is hydrolyzed. Other procedures with protective groups analogous to silane derivatives can also be applied.

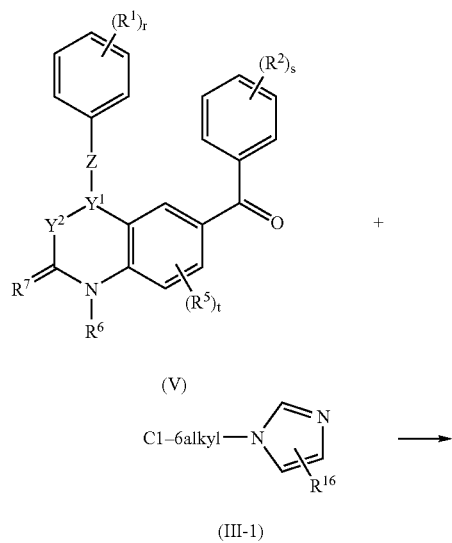

(V)

(III-1)

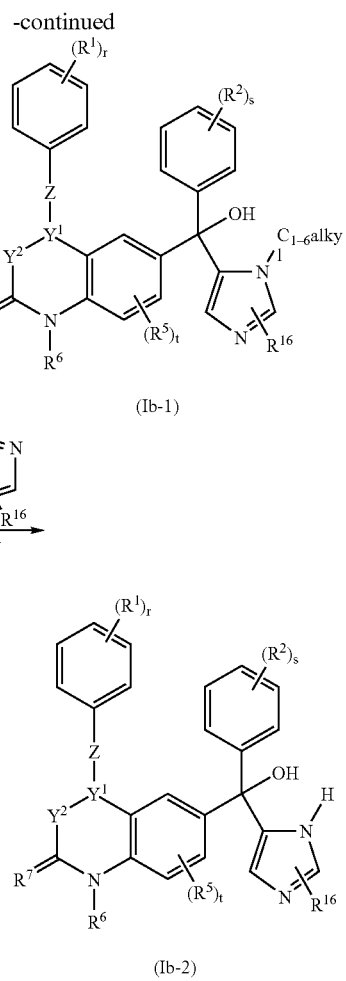

(Ib-1)

(III-2)

(Ib-2)

Also, the compounds of formula (I), wherein $R^4$ is a radical of formula (c-2), $R^3$ is hydroxy and $R^{17}$ is hydrogen, said compounds being referred to as compounds of formula (I-b-2) may be prepared by reacting an intermediate ketone of formula (V) with a intermediate of formula (III-2), wherein PG is a protective group such as, for example, a sulfonyl group, e.g. a dimethylaminosulfonyl group, which can be removed after the addition reaction. Said reaction is conducted analogously as for the preparation of compounds of formula (I-b-1), followed by removal of the protecting group PG, yielding compounds of formula (I-b-2).

Also with regard to process c), the compounds of formula (I) wherein $R^4$ represents a radical of formula (c-3) may be prepared by reacting the compound of formula (IV) with the triazole reagent, preferably in a reaction-inert solvent such as tetrahydrofuran, in the presence of a strong base such as butyl lithium at a temperature ranging from –78° C. to room temperature. When the 3-mercapto derivative is methylated, this is conveniently effected with methyl iodide in the presence of a base such as sodium methylate. Removal of the 3-mercapto group is conveniently effected with sodium nitrite, for example in THF/$H_2O$ in the presence of nitric acid. Removal of the 3-methylmercapto group is conveniently effected with Raney Nickel in ethanol or acetone.

With regard to process e), this may be effected for example as described in WO 97/21701 referred to above, by reacting the nitrone of formula (VI) with the anhydride of a carboxylic acid, e.g. acetic anhydride, thus forming the corresponding ester on the 2-position of the quinoline moiety, which ester can then be hydrolysed in situ to the corresponding quinolinone using a base such potassium carbonate. Alternatively the above nitrone can be reacted with tosyl chloride to prepare the corresponding tosylate which can then be hydrolysed in situ.

Examples of the interconversion of one compound of formula (I) into a different compound of formula (I) include the following reactions:— a) compounds of formula (I-b) can be converted to compounds of formula (I-c), defined as a compound of formula (I) wherein $R^4$ is a radical of formula (c-2) and $R^3$ is hydrogen, by submitting the compounds of formula (I-b) to appropriate reducing conditions, such as, e.g. stirring in acetic acid in the presence of formamide, or treatment with sodium borohydride/trifluoroacetic acid.

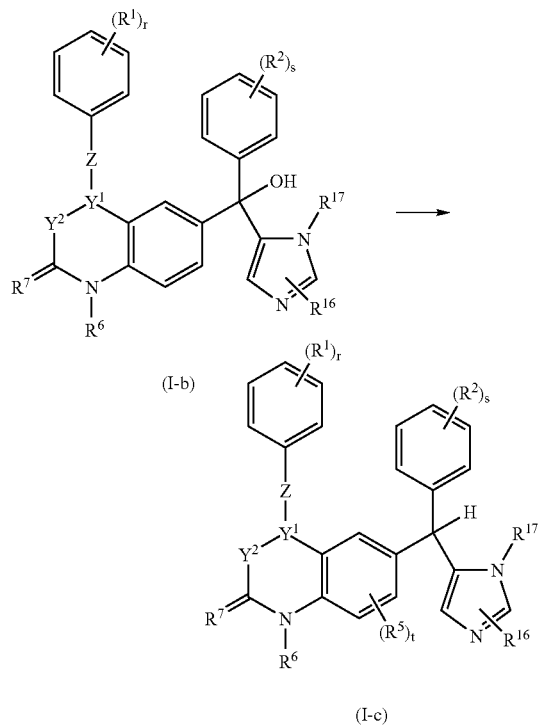

b) compounds of formula (I-b) can be converted to compounds of formula (I-f) wherein $R^3$ is halo, by reacting the compounds of formula (I-b) with a suitable halogenating agent, such as, e.g. thionyl chloride or phosphorus tribromide. Successively, the compounds of formula (I-f) can be treated with a reagent of formula H—$NR^{11}R^{12}$ in a reaction-inert solvent, thereby yielding compounds of formula (I-g).

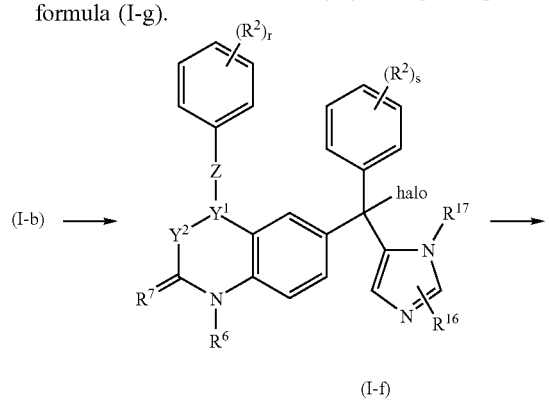

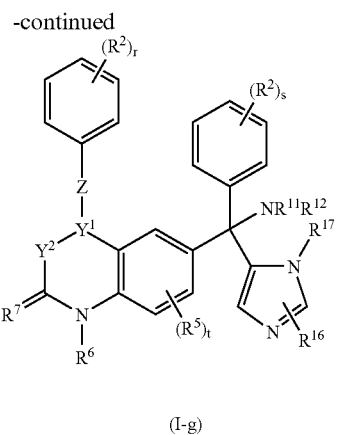

c) compounds of formula (I-b) can be converted into compounds of formula (I-g) for example by treatment with $SOCl_2$, and then $NH_3$/iPrOH, e.g. in a tetrahydrofuran solvent, or by treatment with acetic acid ammonium salt at a temperature ranging from 120 to 180° C., or by treatment with sulfamide at a temperature ranging from 120 to 180° C.;

d) compounds of formula (I-f) can be converted into compounds of formula (I-c) for example by treatment with $SnCl_2$ in the presence of concentrated HCl in acetic acid at reflux;

e) compounds of formula (I) in which X is oxygen can be converted into corresponding compounds of formula (I) in which X is sulphur with a reagent such as phosphorus pentasulfide or Lawesson's reagent in a suitable solvent such as, for example, pyridine;

f) compounds of formula (I) in which $R^9$ is $C_{1-6}$alkyloxycarbonyl can be converted into corresponding compounds of formula (I) in which $R^9$ is hydroxymethyl by conventional reduction procedures for example with the use of lithium aluminium hydride;

g) compounds of formula (I) in which $R^3$ is a radical of formula (b-1) in which $R^{10}$ is hydrogen can be converted into corresponding compounds of formula (I) in which $R^3$ is a radical of formula (b-3) in which $R^{11}$ hydrogen and $R^{12}$ is $C_{1-6}$alkylcarbonyl for example by with an appropriate nitrile for example acetonitrile;

h) compounds of formula (I) in which $R^6$ is hydrogen can be converted into corresponding compounds of formula (I) in which $R^6$ is $C_{1-6}$alkyl for example by treatment with an appropriate alkylating agent, e.g. a $C_{1-6}$ alkyl halide in the presence of a base for example NaH in an appropriate solvent such as THF or DMF.

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitrites to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond.

The intermediates and starting materials used in the above-described processes my be prepared in conventional manner using procedures known in the art for example as described in the above-mentioned patent specifications WO 97/16443, WO 97/21701, WO 98/40383, WO 98/49157 and WO 00/39082.

Thus compounds of formula (III) in which $W^1$ is chloro, used as starting materials in process b), can be prepared, for example in the case where $R^3$ is hydroxy and $R^4$ is a radical of formula (c-2) or (c-3), by reacting a compound of formula (VII):

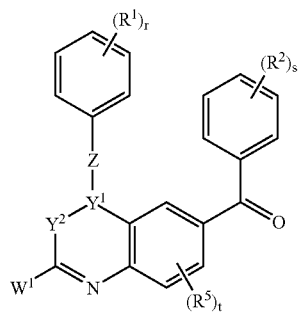
(VII)

with an imidazole, a triazole or a pyridyl reagent in an analogous manner to that described above for process d).

The compound of formula (VII) can be prepared by chlorinating a compound of formula (VIII):

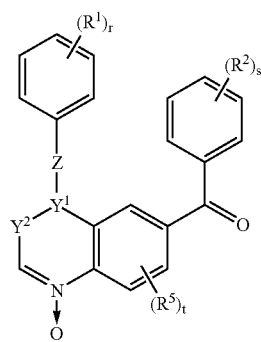
(VIII)

The chlorination of the above compound of formula (VII) can be conveniently effected by treatment with phosphorus oxychloride.

The compound of formula (VIII) can be prepared by oxidising a compound of formula (IX):

The oxidation of the compound of formula (IX) can be effected for example by treatment of

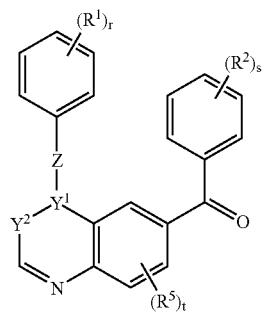
(IX)

the compound with a per-acid such as 3-chloro-benzenecarboperoxoic acid preferably in a reaction-inert solvent such as dichloromethane.

The compound of formula (IX) can be prepared for example from a compound of formula (X):

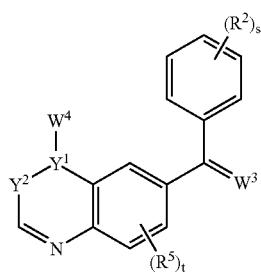
(X)

in which $W^3$ is an oxo group or a protected oxo group such as an ethylenedioxy group and $W^4$ is a leaving group or a precursor group for the moiety (A):

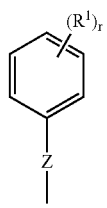
(A)

When $W^4$ is a leaving group, this can be for example a halo e.g. chloro group which can be reacted with a compound of formula:

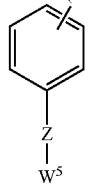

in which $W^5$ is a suitable leaving group: for example when Z is —O—, the leaving group $W^5$ can be hydrogen, and when $W^4$ is chloro, the reaction can be conducted in the presence of sodium hydride preferably in a solvent such as dimethylformamide.

When $W^4$ is a precursor group, this can be for example a methyl group, which can be reacted with a compound of formula

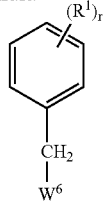

in which $W^6$ is a suitable leaving group such as a halo (e.g. chloro) group to form a compound of formula (I) in which Z is a —$CH_2CH_2$— group; the reaction is advantageously effected in a basic medium for example comprising N-(1-methylethyl)-2-propanamine and N,N,N',N'-tetramethyl-1,2-ethanediamine with butyl lithium in a solvent such as tetrahydrofuran.

The oxo protection can be removed following the reaction of the compound of formula (X) for example by treatment with an acid such as hydrochloric acid in a solvent such as methanol. Alternatively, the oxo protection can be retained to form corresponding oxo-protected forms of the compounds of formulae (VII) or (VIII), such protection being removed after the respective formation of such compounds; the removal may be effected in an analogous manner to that described for the conversion of compounds of formula (X) to compounds of formula (IX).

The compounds of formula (X) used as an intermediates above can be prepared in conventional manner. Thus, when $W^4$ is a methyl group, the compound can be prepared by reacting a compound of formula (XI):

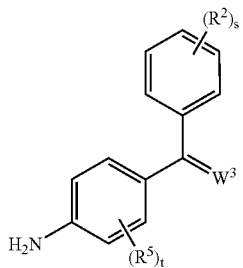

(XI)

with an acid such as hydrochloric acid, then with $FeCl_3$ and $ZnCl_2$ before the addition of 3-buten-2-one. Compounds of formula (X) in which $W^4$ is a different $C_{1-6}$alkyl group can be obtained in analogous manner.

Compounds of formula (X) in which $W^4$ is a chloro group can be obtained by chlorination of the corresponding hydroxy group in a compound of formula (XII):

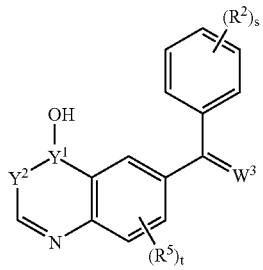

(XII)

Compounds of formula (XII) can be prepared by cyclisation of compounds of formula (XI) in conventional manner.

Compounds of formula (III) in which $W^1$ is a $C_{1-6}$alkyloxy group and $R^3$ is hydroxy can alternatively be prepared for example by reacting a compound of formula (XIII):

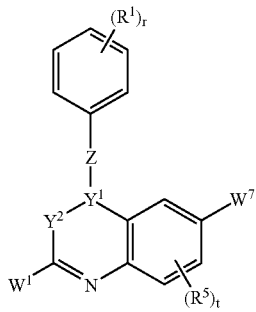

(XIII)

in which $W^7$ is a leaving group for example a halo, e.g. bromo group, with a compound of formula (XIV):

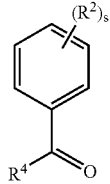

(XIV)

The reaction of the compounds of formulae (XIII) and (XIV) can be conveniently effected in the presence of n-butyl lithium, e.g. in solvent such as tetrahydrofuran.

The above compound of formula (XIII) can be prepared from a corresponding quinolinone compound for example by treatment with $POCl_3$ to form the corresponding 2-chloro compound which can then be reacted with an appropriate $C_{1-6}$alkanol to form the desired 2-$C_{1-6}$alkoxy compound. The starting quinolinone compound can be obtained by a cyclisation reaction as described in the Examples below.

The compounds of formula (IV) used as starting materials in process c) above for example in which $R^3$ is hydrogen and $W^2$ is hydroxy can be prepared by reduction of corresponding compounds of formula (V), used as starting materials for process d); the reduction is conveniently effected by sodium borohydride in a solvent such as methanol. The corresponding compounds of formula (IV) in which $W^2$ is halo for example chloro can be obtained by halogenating the former hydroxy compounds, e.g. with thionyl chloride.

The compounds of formula (V) used as starting materials in process d) can be prepared for example by treatment of a compound of formula (VIII) above in an analogous manner to that described for process e), by reaction with tosyl chloride and subsequent hydrolysis of the resulting tosylate. If desired the resulting compound in which $R^6$ is hydrogen can be converted to a compound with a different $R^6$ group as described above.

Alternatively, compounds of formula (V) can be obtained by cyclisation of a compound of formula (XV):

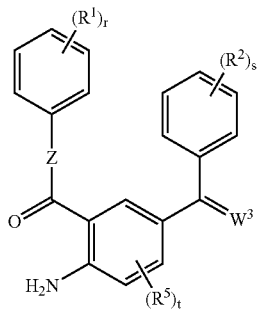

(XV)

and if necessary removing the $W^3$ oxo protection.

The cyclisation of the compound of formula (XV) can be effected in conventional manner for example using procedures analogous to those described in WO 97/16443, advantageously by subjecting the compound of formula (XV) to an acetylation reaction, e.g. by treatment with acetic anhydride in a reaction-inert solvent, e.g. toluene, optionally in the presence of a base to capture acid liberated during the reaction, and subsequent treatment with a base such potassium tert-butoxide in a reaction-inert solvent, e.g. 1,2-dimethoxyethane. The $W^3$ oxo protected group can be converted to the free oxo group in conventional manner, for example as described above.

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a potent farnesyl protein transferase (FPTase) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of tumors in vivo by a direct effect on tumor cell growth but also indirectly, i.e. by facilitating tumor-induced angiogenesis (Rak. J. et al, *Cancer Research*, 55, 4575–4580, 1995). Hence, pharmacologically targeting mutant ras oncogenes could conceivably suppress solid tumor growth in vivo, in part, by inhibiting tumor-induced angiogenesis.

This invention also provides a method for inhibiting tumor growth by administering an effective amount of a compound of the present invention, to a subject, e.g. a mammal (and more particularly a human) in need of such treatment. In particular, this invention provides a method for inhibiting the growth of tumors expressing an activated ras oncogene by the administration of an effective amount of the compounds of the present invention. Examples of tumors which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma (e.g. advanced breast cancer), kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes. With said inhibition being accomplished by the administration of an effective amount of the compounds described herein, to a subject in need of such a treatment. For example, the benign proliferative disorder neuro-fibromatosis, or tumors in which ras is activated due to mutation or overexpression of tyrosine kinase oncogenes, may be inhibited by the compounds of this invention.

The compound according to the invention can be used for other therapeutic purposes, for example:
a) the sensitisation of tumors to radiotherapy by administering the compound according to the invention before, during or after irradiation of the tumor for treating cancer, for example as described in WO 00/01411;
b) treating athropathies such as rheumatoid arthritis, osteoarthritis, juvenile arthritis, gout, polyarthritis, psoriatic arthritis, ankylosing spondylitis and systemic lupus erythematosus, for example as described in WO 00/01386;
c) inhibiting smooth muscle cell proliferation including vascular proliferative disorders, atherosclerosis and restenosis, for example as described in WO 98/55124;
d) treating inflammatory conditions such as ulcerative colitis, Crohn's disease, allergic rhinitis, graft vs host disease, conjunctivitis, asthma, ARDS, Behcets disease, transplant rejection, uticaria, allergic dermatitis, alopecia areata, scleroderma, exanthem, eczema, dermatomyositis, acne, diabetes, systemic lupus erythematosis, Kawasaki's disease, multiple sclerosis, emphysema, cystic fibrosis and chronic bronchitis;
e) treating endometriosis, uterine fibroids, dysfunctional uterine bleeding and endometrial hyperplasia;
f) treating ocular vascularisation including vasculopathy affecting retinal and choroidal vessels;
g) treating pathologies resulting from heterotrimeric G protein membrane fixation including diseases related to following biological functions or disorders; smell, taste, light, perception, neurotransmission, neurodegeneration, endocrine and exocrine gland functioning, autocrine and paracrine regulation, blood pressure, embryogenesis, viral infections, immunological functions, diabetes, obesity;
h) inhibiting viral morphogenesis for example by inhibiting the prenylation or the post-prenylation reactions of a viral protein such as the large delta antigen of hepatitis D virus; and the treatment of HIV infections;
i) treating polycystic kidney disease;
j) suppressing induction of inducible nitric oxide including nitric oxide or cytokine mediated disorders, septic shock, inhibiting apoptosis and inhibiting nitric oxide cytotoxicity;
k) treating malaria.

The compounds of present invention may be useful for the treatment of proliferative diseases, both benign and malignant, wherein the K-ras B isoform is activated as a result of oncogenic mutation.

Hence, the present invention discloses the compounds of formula (I) for use as a medicine as well as the use of these compounds of formula (I) for the manufacture of a medicament for treating one or more of the above-mentioned conditions.

For the treatment of the above conditions, the compound of the invention may be advantageously employed in combination with one or more other medicinal agents such as anti-cancer agents
for example selected from platinum coordination compounds for example cisplatin or carboplatin, taxane compounds for example paclitaxel or docetaxel, camptothecin compounds for example irinotecan or topotecan, anti-tumor vinca alkaloids for example vinblastine, vincristine or vinorelbine, anti-tumor nucleoside derivatives for example 5-fluorouracil, gemcitabine or capecitabine, nitrogen mustard or nitrosourea alkylating agents for example cyclophosphamide, chlorambucil, carmustine or lomustine, anti-tumor anthracycline derivatives for example daunorubicin, doxorubicin or idarubicin; HER2 antibodies for example trastzumab; and anti-tumor podophyllotoxin derivatives for example etoposide or teniposide; and antiestrogen agents including estrogen receptor antagonists or selective estrogen receptor modulators preferably tamoxifen, or alternatively toremifene, droloxifene, faslodex and raloxifene, or aromatase inhibitors such as exemestane, anastrozole, letrazole and vorozole.

For the treatment of cancer the compounds according to the present invention can administered to a patient as described above in conjunction with irradiation; such treatment is may be especially beneficial as farnesyl transferase inhibitors can act as radiosensitisers for example as described in International Patent Specification WO 00/01411, enhancing the therapeutic effect of such irradiation.

Irradiation means ionizing radiation and in particular gamma radiation, especially that emitted by linear accelerators or by radionuclides that are in common use today. The irradiation of the tumor by radionuclides can be external or internal.

Preferably, the administration of the farnesyl transferase inhibitor commences up to one month, in particular up to 10 days or a week, before the irradiation of the tumor. Additionally, it is advantageous to fractionate the irradiation of the tumor and maintain the administration of the farnesyl transferase inhibitor in the interval between the first and the last irradiation session.

The amount of farnesyl protein transferase inhibitor, the dose of irradiation and the intermittence of the irradiation doses will depend on a series of parameters such as the type of tumor, its location, the patients' reaction to chemo- or radiotherapy and ultimately is for the physician and radiologists to determine in each individual case.

The present invention also concerns a method of cancer therapy for a host harboring a tumor comprising the steps of
administering a radiation-sensitizing effective amount of a farnesyl protein transferase inhibitor according to the invention before, during or after
administering radiation to said host in the proximity to the tumor.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which
additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.01 mg/kg to 100 mg/kg body weight, and in particular from 0.05 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 1 mg to 200 mg of active ingredient per unit dosage form.

Experimental Part

Hereinafter "THF" means tetrahydrofuran, "DIPE" means diisopropyl ether, "EtOAc" means ethyl acetate, "DCM" means dichloromethane, "DMF" means dimethylformamide and "BuLi" means n-butyl lithium, "BTEAC" means benzyltriethylammonium salt.

A. Preparation of the Intermediates

EXAMPLE A1 a) (4-aminophenyl)(4-chlorophenyl)-methanone (0.104 mol) and diethyl (ethoxymethylene) malonate (0.114 mol) were stirred and heated at 130° C. overnight. The product was used without further purification, yielding ethyl 2-[[[4-(4-chlorobenzoyl)phenyl]amino]carbonyl]-3-ethoxy-2-propenoate (intermediate 1).
b) A mixture of intermediate 1 (0.104 mol) in 1-1'-oxybisbenzene (100 ml) was stirred and heated at 300° C. for 8 h. The mixture was taken up in diethyl ether and the product was filtered off giving 14.6 g (39.5%) of ethyl 6-(4-chlorobenzoyl)-4-hydroxy-3-quinolinecarboxylate, melting point >300° C. (intermediate 2).
c) A mixture of intermediate 2 (0.051 mol) in sodium hydroxide (35 ml) and water (100 ml) was stirred and refluxed overnight. The mixture was cooled and poured onto $H_2O$. The pH of the mixture was brought to 7 by adding HCl 6N and the mixture was filtered off. The precipitate was washed with diethyl ether, taken up in DCM and filtered off. The product was used without further purification, yielding 16 g of 6-(4-chlorobenzoyl)-4-hydroxy-3-quinolinecarboxylic acid (intermediate 3).
d) Intermediate 3 (0.039 mol), Cu powder (0.031 mol) and quinoline (0.465 mol) were stirred at 250° C. for 1 h 15 min. The mixture was cooled, taken up in DCM and washed with water. The organic layer was dried ($MgSO_4$), filtered off and evaporated till dryness. The residue was taken up in diethyl ether, filtered off and dried, yielding 7.9 g (71%) of (4-chlorophenyl) (4-hydroxy-6-quinolinyl) methanone (intermediate 4).
e) A mixture of intermediate 4 (0.027 mol) in phosphoryl chloride (100 ml) was stirred at 60° C. for 3 h. The mixture was evaporated, the residue was taken up in DCM and basified with $K_2CO_3$ 10%. The organic layer was dried ($MgSO_4$), filtered off and evaporated. The product was used without further purification, yielding 7.6 g (91%) of (4-chlorophenyl)(4-chloro-6-quinolinyl)methanone (intermediate 5).
f) A mixture of phenol (0.026 mol) and sodium hydride (0.035 mol) in DMF (15 ml) was stirred at room temperature for 1 h. intermediate 5 (0.025 mol) was added portionwise at room temperature, then DMF (80 ml) was added dropwise and the mixture was stirred at room temperature overnight. Water was added and the mixture was evaporated. The residue was taken up in DCM and washed with water. The organic layer was dried ($MgSO_4$), filtered off and evaporated till dryness. The product was used without further purification, yielding (4-chlorophenyl)(4-phenoxy-6-quinolinyl)methanone (intermediate 6).
g) A mixture of intermediate 6 (0.025 mol) and 3-chlorobenzenecarboperoxoic acid (0.05 mol) in DCM (150 ml) was stirred at room temperature for 12 h. The mixture was basified with a solution of $K_2CO_3$ 10% and extracted with DCM. The organic layer was dried ($MgSO_4$), filtered off and evaporated till dryness. The product was used without further purification, yielding (4-chlorophenyl)(4-phenoxy-6-quinolinyl)methanone,N-oxide (intermediate 7).
h) A mixture of intermediate 7 (0.025 mol), 4-methylbenzenesulfonyl chloride (0.0312 mol) in $K_2CO_3$ 10% (100 ml) and DCM (100 ml) was stirred at room temperature for 12 h. The organic layer was decanted, dried ($MgSO_4$), filtered off and evaporated till dryness. The residue was taken up in diethyl ether, the precipitate was filtered off and dried, yielding 5 g (53%) of 6-(4-chlorobenzoyl)-4-phenoxy-2(1H)-quinolinone (intermediate 8).
i) Sodium tetrahydroborate (0.0159 mol) was added portionwise at room temperature to a solution of intermediate 8 (0.0133 mol) in methanol (50 ml) and the mixture was stirred at room temperature for 1 h. Water was added and the mixture was evaporated. The precipitate was filtered off, washed with water and diethyl ether and dried, yielding 4 g (80%) of (±)-6-[(4-chlorophenyl)hydroxymethyl]-4-phenoxy-2(1H)-quinolinone (intermediate 9).

EXAMPLE A2 a) HCl/diethylether (0.15 mol) was added dropwise to a solution of (4-aminophenyl)(4-chlorophenyl)-methanone (0.15 mol) in ethanol (250 ml) and the mixture was stirred for 15 min. $FeCl_3.6H_2O$ (0.255 mol) and then $ZnCl_2$ (0.015 mol) were added and the mixture was stirred at 65° C. for 30 min. 3-buten-2-one (0.15 mol) was added and the mixture was stirred at 80° C. overnight. The mixture was poured into ice and basified with $NH_4OH$. The suspension was filtered through celite and the filtrate was extracted with DCM. The organic layer was dried ($MgSO_4$), filtered off and evaporated till dryness. The product was used without further purification, yielding 43.1 g (100%) of (4-chlorophenyl)(4-methyl-6-quinolinyl)-methanone, mp 114° C. (intermediate 10).
b) A mixture of intermediate 10 (0.15 mol), 1,2-ethanediol (0.54 mol) and paratoluenesulfonic acid (0.18 mol) in toluene (600 ml) was stirred and refluxed in a Dean Stark apparatus overnight. The mixture was cooled, basified with $K_2CO_3$ 10% and extracted with DCM. The organic layer was dried ($MgSO_4$), filtered off and evaporated till dryness. The residue was purified by column chromatography over silica gel (eluent: $CH_2Cl_2/CH_3OH/NH_4OH$ 99.75/0.25/0.2) (35–70 μm). The pure fractions were collected and evaporated, yielding 35 g (73%) of 6-[2-(4-chlorophenyl)-1,3-dioxolan-2-yl]-4-methyl-quinoline (intermediate 11).
c) BuLi (0.0612 mol) was added dropwise to a cooled (−20° C.) solution of N,N,N',N'-tetramethyl-1,2-ethanediamine (0.0612 mol) and N-(1-methylethyl)-2-propanamine (0.0612 mol) in THF (20 ml) and the mixture was stirred at −20° C. for 15 min. A solution of intermediate 11 (0.0408 mol) in THF (45 ml) was added slowly and the mixture was stirred at −20° C. for 1 h. 1-chloro-3-(chloromethyl)-benzene (0.049 mol) was added and the mixture was stirred at room temperature overnight. The mixture was quenched with water and extracted with EtOAc. The organic layer was dried ($MgSO_4$), filtered off and evaporated till dryness. The residue was purified by column chromatography over silica gel (eluent: cyclohexane/EtOAc 70/30) (15–40 μm). The pure fractions were collected, yielding 3.9 g of 6-[2-(4-chlorophenyl)-1,3-dioxolan-2-yl]-4-[2-(3-chlorophenyl)ethyl]-quinoline (intermediate 12a) and 3.9 g of 4-[2-(3-chlorophenyl)-1-[(3-chlorophenyl)methyl]ethyl]-6-[2-(4-chlorophenyl)-1,3-dioxolan-2-yl]-quinoline (intermediate 12b).
d) 3-chlorobenzenecarboperoxoic acid (0.042 mol) was added to a mixture of intermediate 12a (0.021 mol) in DCM (100 ml). The mixture was stirred at room temperature for 1 hour. $K_2CO_3$ 10% was added. The mixture was extracted with DCM. The organic layer was separated, dried ($MgSO_4$), filtered and the solvent was evaporated. The product was used without further purification, yielding 6-[2-(4-chlorophenyl)-1,3-dioxolan-2-yl]-4-[2-(3-chlorophenyl)ethyl]-, 1-oxide quinoline (intermediate 13).

e) $K_2CO_3$ 10% (150 ml) and then 4-methyl-benzenesulfonyl chloride (0.0315 mol) were added to a mixture of intermediate 13 (0.021 mol) in DCM (150 ml). The mixture was stirred at room temperature for 1 hour. Diethylether was added. The mixture was decanted and extracted with DCM. The organic layer was separated, dried ($MgSO_4$), filtered and the solvent was evaporated. The residue was crystallized from diethylether. The precipitate was filtered off and dried, yielding 7 g (71%) of 6-[2-(4-chlorophenyl)-1,3-dioxolan-2-yl]-4-[2-(3-chlorophenyl)ethyl]-2(1H)-quinolinone (intermediate 14).

f) BTEAC (0.0015 mol) and then iodomethane (0.03 mol) were added to a mixture of intermediate 14 (0.015 mol) in concentrated sodium hydroxide (50 ml) and THF (50 ml). The mixture was stirred at room temperature for the weekend. Water was added and the mixture was extracted with DCM. The organic layer was dried ($MgSO_4$), filtered and the solvent was evaporated, yielding 7.5 g (>100%) of 6-[2-(4-chlorophenyl)-1,3-dioxolan-2-yl]-4-[2-(3-chlorophenyl)ethyl]-1-methyl-2(1H)-quinolinone (intermediate 15).

g) A mixture of intermediate 15 (0.015 mol) in HCl 3N (70 ml) and THF (70 ml) was stirred and refluxed overnight. Water was added and the mixture was extracted with DCM. The organic layer was separated, dried ($MgSO_4$), filtered, and the solvent was evaporated. The residue was crystallized from acetonitrile. The precipitate was filtered off, washed with DIPE and dried, yielding 4.5 g (69%) of 6-(4-chlorobenzoyl)-4-[2-(3-chlorophenyl)ethyl]-1-methyl-2(1H)-quinolinone (intermediate 16).

EXAMPLE A3 a) A mixture of 2-(4-chlorophenyl)-2-(4-nitrophenyl)-1,3-dioxolane (described in WO 97/16443) (0.164 mol) in methanol (500 ml) was hydrogenated under a 3 bar pressure for 3 hours with Raney Nickel (50 g) as a catalyst. After uptake of $H_2$ (3 equiv), the catalyst was filtered through celite and the filtrate was evaporated till dryness. The reaction was carried out again using the same quantities. The residues were combined and used without further purification, yielding 88 g (97.3%) of 4-[2-(4-chlorophenyl)-1,3-dioxolan-2-yl]-benzenamine (intermediate 17).

b) Intermediate 17 (0.32 mol) and (ethoxymethylene)-1-propanedioic acid, diethyl ester (0.352 mol) were stirred at 130° C. overnight using a Dean-Stark apparatus and then cooled to room temperature. DCM was added. The organic solution was washed with water, dried ($MgSO_4$), filtered and the solvent was evaporated till dryness. The residue (160 g) was purified by column chromatography over silica gel (eluent: cyclohexane/EtOAc 75/25; 15–40 μm). The pure fractions were collected and the solvent was evaporated, yielding 120 g (82.7%) of 2-[[[4-[2-(4-chlorophenyl)-1,3-dioxolan-2-yl]phenyl]amino]carbonyl]-3-ethoxy-(2Z)-2-propenoic acid ethyl ester (intermediate 18).

c) A mixture of intermediate 18 (0.09 mol) in 1,1'-oxybis-benzene (110 ml) was stirred at 300° C. for 20 hours and then cooled. DIPE and petroleum ether were added. The precipitate was filtered off, washed and dried. The reaction was carried out again using the same quantities. The residues were combined and purified by column chromatography over silica gel (eluent: $CH_2Cl_2/CH_3OH$ 96/4; 15–40 μm). The pure fractions were collected and the solvent was evaporated, to give 11.5 g of 6-[2-(4-chlorophenyl)-1,3-dioxolan-2-yl]-4-hydroxy-3-quinolinecarboxylic acid ethyl ester (intermediate 19).

d) A mixture of intermediate 19 (0.0175 mol) in phosphoryl chloride (70 ml) was stirred at 60° C. for 2 hours and then cooled. The solvent was evaporated till dryness. The residue was taken up in DCM. The organic solution was washed with $K_2CO_3$ 10%, dried ($MgSO_4$), filtered and the solvent was evaporated. The product was used without further purification, yielding 8.1 g of 4-chloro-6-[2-(4-chlorophenyl)-1,3-dioxolan-2-yl]-3-quinolinecarboxylic acid ethyl ester (intermediate 20).

e) Sodium hydride (0.0298 mol) was added at 10° C. under $N_2$ flow to a solution of 3-chloro-phenol (0.0193 mol) in DMF (50 ml). The mixture was stirred for 1 hour. A solution of intermediate 20 (0.0175 mol) in DMF (50 ml) was added dropwise. The mixture was stirred at room temperature for 3 hours, poured out into water and extracted with EtOAc. The organic layer was separated, washed with water, dried ($MgSO_4$), filtered and the solvent was evaporated. The product was used without further purification, yielding 9.01 g of 4-(3-chlorophenoxy)-6-[2-(4-chlorophenyl)-1,3-dioxolan-2-yl]-3-quinolinecarboxylic acid, ethyl ester (intermediate 21).

f) 3-chlorobenzenecarboperoxoic acid was added at room temperature to a mixture of intermediate 21 (0.0175 mol) in DCM (100 ml). The mixture was stirred at room temperature overnight. $K_2CO_3$ 10% was added. The organic layer was separated, dried ($MgSO_4$), filtered and used as such without further purification, yielding 4-(3-chlorophenoxy)-6-[2-(4-chlorophenyl)-1,3-dioxolan-2-yl]-3-quinolinecarboxylic acid, ethyl ester, 1-oxide (intermediate 22).

g) $K_2CO_3$ 10% (150 ml) was added to a solution of intermediate 22 (0.0175 mol) in DCM (150 ml). Then 4-methyl-benzenesulfonyl chloride (0.0219 mol) was added. The mixture was stirred at room temperature for 4 hours. The organic layer was separated, washed with water, dried ($MgSO_4$), filtered and the solvent was evaporated. The product was used without further purification, yielding 13 g of 4-(3-chlorophenoxy)-6-[2-(4-chlorophenyl)-1,3-dioxolan-2-yl]-1,2-dihydro-2-oxo-3-quinolinecarboxylic acid ethyl ester (intermediate 23).

h) A mixture of intermediate 23 (0.0175 mol) in HCl 3N (140 ml) and THF (30 ml) was stirred and refluxed for 4 hours, then cooled, poured out into water and extracted with EtOAc. The organic layer was separated, washed with $K_2CO_3$ 10%, dried ($MgSO_4$), filtered and the solvent was evaporated. The residue (11.4 g) was purified by column chromatography over silica gel (eluent: $CH_2Cl_2/CH_3OH$ 97.5/2.5; 20–45 μm). The pure fractions were collected and the solvent was evaporated yielding 6.4 g (76%) of 6-(4-chlorobenzoyl)-4-(3-chlorophenoxy)-1,2-dihydro-2-oxo-3-quinolinecarboxylic acid, ethyl ester (intermediate 24).

i) Sodium tetrahydroborate (0.034 mol) was added portionwise at 10° C. to a solution of intermediate 24 (0.017 mol) in methanol (100 ml). The mixture was stirred for 1 hour. Water was added and the mixture was extracted with DCM. The organic layer was separated, dried ($MgSO_4$), filtered and the solvent was evaporated, yielding 7.5 g (91%) of 4-(3-chlorophenoxy)-6-[(4-chlorophenyl)hydroxymethyl]-1,2-dihydro-2-oxo-3-quinolinecarboxylic acid, ethyl ester (intermediate 25).

j) A mixture of intermediate 25 (0.0155 mol) in thionyl chloride (75 ml) was stirred and refluxed for 24 hours and then cooled. The solvent was evaporated till dryness. The product was used without further purification, yielding 6-[chloro(4-chlorophenyl)methyl]-4-(3-chlorophenoxy)-1,2-dihydro-2-oxo-3-quinolinecarboxylic acid, ethyl ester (intermediate 26).

EXAMPLE A4 a) A mixture of intermediate 12a (0.0087 mol) and intermediate 12b (0.0087 mol) in HCl 3N (80 ml) and methanol (30 ml) was stirred and refluxed overnight. The mixture was poured into ice, basified with $NH_4OH$ and extracted with DCM. The organic layer was dried ($MgSO_4$), filtered off and evaporated till dryness. The residue was purified by column chromatography over silica gel (eluent: $CH_2Cl_2$/EtOAc 96/4) (15–40 µm). The pure fractions were collected and evaporated, yielding 2.4 g (34%) (4-chlorophenyl)[4-[2-(3-chlorophenyl)ethyl]-6-quinolinyl]-methanone (intermediate 27a) and 2.8 g (44%) of (4-chlorophenyl)[4-[2-(3-chlorophenyl)-1-[(3-chlorophenyl)methyl]ethyl]-6-quinolinyl]-methanone (intermediate 27b).

b) 3-chloro-benzenecarboperoxoic acid (0.0129 mol) was added to a solution of intermediate 27a (0.0059 mol) in DCM (25 ml) and the mixture was stirred at room temperature for 1 h. A solution of $K_2CO_3$ 10% was added and the mixture was extracted with DCM. The organic layer was dried ($MgSO_4$), filtered off and evaporated till 50 ml of the solvent which was used without further purification, yielding (quant.) of (4-chlorophenyl)[4-[2-(3-chlorophenyl)ethyl]-1-oxido-6-quinolinyl]-methanone (intermediate 28).

c) A mixture of intermediate 28 (0.0337 mol) in phosphoryl chloride (100 ml) was stirred and refluxed for 30 min. The solvent was evaporated till dryness. The residue was taken up in ice and $NH_4OH$. The mixture was stirred for 3 hours and extracted with DCM. The organic layer was separated, dried ($MgSO_4$), filtered and the solvent was evaporated till dryness. The residue (14.2 g) was purified by column chromatography over silica gel (eluent: cyclohexane/EtOAc 90/10; 20–45 µm). The pure fractions were collected and the solvent was evaporated. The residue was taken up in DCM and a small amount of methanol. The precipitate was filtered off and dried, yielding 7.45 g (50%) of [2-chloro-4-[2-(3-chlorophenyl)ethyl]-6-quinolinyl](4-chlorophenyl)-methanone, melting point 180° C. (intermediate 29).

d) BuLi 1.6M in hexane was added dropwise at –70° C. to a mixture of 1-methyl-1H-imidazole (0.0098 mol) in TBF (15 ml). The mixture was stirred for 30 min. $ClSiEt_3$ (0.0098 mol) was added. The mixture was brought slowly to 10° C. and cooled again to –70° C. BuLi 1.6M in hexane (6.1 ml) was added dropwise. The mixture was stirred for 1 hour, brought quickly to –15° C. and cooled again to –70° C. A solution of intermediate 29 (0.0082 mol) in THF (40 ml) was added dropwise. The mixture was stirred at –50° C., then hydrolyzed and extracted with EtOAc. The organic layer was separated, dried ($MgSO_4$), filtered and the solvent was evaporated till dryness. The residue (5.4 g) was purified by column chromatography over silica gel (eluent: toluene/2-propanol/$NH_4OH$ 87/13/0.5; 15–40 µm). The pure fractions were collected and the solvent was evaporated, yielding 2.15 g (50%) of 2-chloro-α-(4-chlorophenyl)-4-[2-(3-chlorophenyl)ethyl]-α-(1-methyl-1H-imidazol-5-yl)-6-quinolinemethanol (intermediate 30).

EXAMPLE A5 a) BuLi (0.058 mol) was added dropwise at –20° C. to a solution of N-(1-methylethyl)-2-propanamine (0.058 mol) and N,N,N',N'-tetramethyl-1,2-ethanediamine (0.058 mol) in THF (95 ml) and the mixture was stirred at –20° C. for 15 min. A solution of intermediate 11 (0.0387 mol) in THF (13 ml) was added dropwise at –20° C. and the mixture was stirred at –20° C. for 1 h. (Chloromethyl)-benzene (0.0464 mol) was added at –20° C. and the mixture was heated till room temperature. The mixture was hydrolysed and evaporated till dryness. The residue was taken up in DCM and $K_2CO_3$ 10%. The organic layer was dried ($MgSO_4$), filtered off and evaporated till dryness. The residue was purified by column chromatography over silica gel (eluent: cyclohexane/EtOAc 60/40) (35–70 µm). The pure fractions were collected and evaporated, yielding 9 g (56%) of 6-[2-(4-chlorophenyl)-1,3-dioxolan-2-yl]-4-(2-phenylethyl)-quinoline (intermediate 31).

b) A mixture of intermediate 31 (0.0216 mol) in HCl 3N (50 ml) and methanol (50 ml) was stirred at 60° C. overnight. The mixture was basified with $NH_4OH$ and extracted with DCM. The organic layer was dried ($MgSO_4$), filtered off and evaporated till dryness. The product was used without further purification, yielding 6.5 g (80%) of (4-chlorophenyl)[4-(2-phenylethyl)-6-quinolinyl]-methanone (intermediate 32).

c) A mixture of intermediate 32 (0.0175 mol) and 3-chlorobenzenecarboperoxoic acid (0.035 mol) in DCM (100 ml) was stirred at room temperature for 3 h. The mixture was basified with a solution of $K_2CO_3$ 10%. The organic layer was dried ($MgSO_4$), filtered off and evaporated till dryness. The product was used without further purification, yielding 6.7 g (100%) of (4-chlorophenyl)[1-oxido-4-(2-phenylethyl)-6-quinolinyl]-methanone (intermediate 33).

d) A mixture of intermediate 33 (0.0242 mol) in phosphoryl chloride (100 ml) was stirred and refluxed for 1 hour. The solvent was evaporated till dryness. The residue was taken up in DCM. The mixture was poured out into ice water and basified with $NH_4OH$. The organic layer was separated, dried ($MgSO_4$), filtered and the solvent was evaporated till dryness. The residue was crystallized from 2-propanone. The precipitate was filtered off, washed with diethyl ether and dried, yielding 4.8 g (49%) of (4-chlorophenyl)[2-chloro-4-(2-phenylethyl)-6-quinolinyl]-methanone (intermediate 34).

e) BuLi 1.6M in hexane (8.9 ml) was added dropwise at –70° C. under $N_2$ flow to a mixture of 1-methyl-1H-imidazole (0.0118 mol) in THF (20 ml). The mixture was stirred for 30 min. $ClSiEt_3$ (0.0142 mol) was added. The mixture was brought slowly to room temperature and cooled again to –70° C. C (8.9 ml) was added dropwise. The mixture was stirred for 1 hour, brought quickly to –20° C. and cooled again to –70° C. A solution of intermediate 34 (0.0118 mol) in THF (50 ml) was added dropwise. The mixture was stirred at –70° C. for 1 hour, hydrolyzed and extracted with DCM. The organic layer was separated, dried ($MgSO_4$), filtered and the solvent was evaporated till dryness. The residue (8.8 g) was purified by column chromatography over silica gel (eluent: toluene/2-propanol/$NH_4OH$ 85/15/0.5; 20–45 µm). Two pure fractions were collected and their solvents were evaporated, yielding 1.7 g (35%) of starting material intermediate 34 and 2.3 g (40%) of 2-chloro-α-(4-chlorophenyl)-α-(1-methyl-1H-imidazol-5-yl)-4-(2-phenylethyl)-6-quinolinemethanol (intermediate 35).

EXAMPLE A6 a) 4-Methylbenzenesulfonate (0.0364 mol) and then trimethoxy-methane (3.636 mol) were added to a mixture of 5-bromo-1H-indole-2,3-dione (0.364 mol) in methanol (1200 ml). The mixture was stirred and refluxed for 3 hours, poured out into ice water and extracted with DCM. The organic layer was separated, dried ($MgSO_4$), filtered and the solvent was evaporated till dryness. The residue (125 g) was purified by column chromatography over silica gel (eluent: $CH_2Cl_2/CH_3OH$ 99/1 and 98/2; 20–45 µm). The pure fractions were collected and the solvent was evaporated. The residue (50 g, 52%) was taken up in DIPE. The precipitate was filtered off and dried, yielding 45 g (45%) of 5-bromo-1,3-dihydro-3,3-dimethoxy-2H-indol-2-one (intermediate 36).

b) BuLi 1.6M in hexane (0.127 mol) was added dropwise at −70° C. to a mixture of intermediate 36 (0.0577 mol) in THF (150 ml). The mixture was stirred for 1 hour. A solution of 4-chloro-N-methoxy-N-methyl-benzamide (0.0634 mol) in THF (30 ml) was added dropwise. The mixture was brought to room temperature, stirred at room temperature for 3 hours, hydrolysed and extracted with DCM. The organic layer was separated, dried ($MgSO_4$), filtered and the solvent was evaporated till dryness. The residue was crystallized from 2-propanone and diethyl ether. The precipitate was filtered off, washed with DIPE and dried, yielding 8.05 g (42%) of 5-(4-chlorobenzoyl)-1,3-dihydro-3,3-dimethoxy-2H-indol-2-one, melting point 170° C. (intermediate 37).

c) A mixture of intermediate 37 (0.151 mol) in HCl 3N (300 ml) and THF (300 ml) was stirred and refluxed overnight and then cooled. The solvent was evaporated partially. The precipitate was filtered off, washed several times with diethyl ether and dried with toluene in vacuo, yielding 40 g (93%) of 5-(4-chlorobenzoyl)-1H-indole-2,3-dione (intermediate 38).

d) A mixture of intermediate 38 (0.119 mol) in acetic anhydride (150 ml) was stirred and refluxed for 1 hour and then cooled. DIPE was added. The precipitate was filtered off, washed several times with DIPE and dried, yielding 35.5 g (91%) of 1-acetyl-5-(4-chlorobenzoyl)-1H-indole-2,3-dione (intermediate 39).

e) A mixture of intermediate 39 (0.078 mol), propanedioic acid (0.094 mol) and NaOAc (0.0094 mol) in HOAc (140 ml) was stirred and refluxed for 48 hours and then cooled. Water was added. The precipitate was filtered off, washed several times with water and dried with toluene in vacuo. The reaction was carried out three times. The residues were combined, yielding 72.9 g (95%) of 6-(4-chlorobenzoyl)-1,2-dihydro-2-oxo-4-quinolinecarboxylic acid, melting point >260° C. (intermediate 40).

f) 1-(3-Dimethylaminopropyl)-3-ethyl-carbodiimide hydrochloride (0.037 mol), 1-hydroxybenzotriazole (0.037 mol) and triethylamine (0.037 mol) were added at room temperature to a solution of intermediate 40 (0.0244 mol) and 3-chloro-benzenamide (0.037 mol) in THF (240 ml) under $N_2$ flow. The mixture was stirred at room temperature for 24 hours, poured out into ice water and extracted with EtOAc. The organic layer was separated, dried ($MgSO_4$), filtered, and the solvent was evaporated. The residue (11 g) was purified by column chromatography over silica gel (eluent: $CH_2Cl_2/CH_3OH/NH_4OH$ 95/5/0.5; 15–35 µm). The pure fractions were collected and the solvent was evaporated, yielding: 3.2 g (30%). Part of this fraction (0.2 g) was crystallized from $CH_2Cl_2$/diethyl ether. The precipitate was filtered off and dried, yielding 0.16 g of 6-(4-chlorobenzoyl)-N-(3-chlorophenyl)-1,2-dihydro-2-oxo-4-quinolinecarboxamide hydrate (1:1), melting point 214° C. (intermediate 41).

g) A mixture of intermediate 41 (0.0059 mol), iodomethane (0.0088 mol) and BTEAC (0.0003 mol) in NaOH 3N (30 ml) and THF (30 ml) was stirred at room temperature for 6 hours, poured out into water and extracted with EtOAc. The organic layer was separated, dried ($MgSO_4$), filtered, and the solvent was evaporated. The residue (2.4 g) was purified by column chromatography over silica gel (eluent: $CH_2Cl_2/CH_3OH/NH_4OH$ 98.5/1.5 to 95/5/0.2; 15–40 µm). The pure fractions were collected and the solvent was evaporated, yielding: 0.98 g (35%) of a residue. A sample of the residue (0.75 g) was crystallized from $CH_3CN$/diethyl ether. The precipitate was filtered off and dried, yielding 0.585 g of 6-(4-chlorobenzoyl)-N-(3-chlorophenyl)-1,2-dihydro-N,1-dimethyl-2-oxo-4-quinolinecarboxamide, melting point 184° C. (intermediate 42).

EXAMPLE A7 a) A mixture of 1-(3-dimethylaminopropyl)-3-ethyl-carbodiimide hydrochloride (0.037 mol), 1-hydroxybenzotriazole (0.037 mol) and triethylamine (0.037 mol) was added at room temperature to a solution of intermediate 40 (0.0244 mol) and 3-methyl-benzenamine (0.037 mol) in THF (240 ml) under $N_2$ flow. The mixture was stirred at room temperature for 24 hours, poured out into ice water and extracted with EtOAc. The organic layer was separated, dried ($MgSO_4$), filtered, and the solvent was evaporated. Part (0.2 g) of the residue (7.3 g, 72%) was crystallized from $CH_2Cl_2$/diethyl ether. The precipitate was filtered off and dried, yielding 0.16 g of 6-(4-chlorobenzoyl)-1,2-dihydro-N-(3-methylphenyl)-2-oxo-4-quinolinecarboxamide, melting point 230° C. (intermediate 43).

b) A mixture of intermediate 43 (0.017 mol), iodomethane (0.034 mol) and BTEAC (0.0008 mol) in NaOH 3N (70 ml) and THF (70 ml) was stirred at room temperature for 5 hours and poured out into ice water. EtOAc was added. The mixture was filtered over celite. The organic layer was separated, dried ($MgSO_4$), filtered, and the solvent was evaporated. The residue was taken up in $CH_2Cl_2$/diethyl ether. The precipitate was filtered off and discarded. The filtrate was evaporated and the residue (4.1 g) was purified by column chromatography over silica gel (eluent: $CH_2Cl_2/CH_3OH$ 98.5/1.5; 15–40 µm). The pure fractions were collected and the solvent was evaporated, yielding: 2.18 g of a residue which was further purified by column chromatography over silica gel (eluent: toluene/$CH3OH$ 95/5; 15–40 µm). The pure fractions were collected and the solvent was evaporated, yielding: 1.9 g (25%) of 6-(4-chlorobenzoyl)-1,2-dihydro-N,1-dimethyl-N-(3-methylphenyl)-2-oxo-4-quinolinecarboxamide, melting point 91° C. (intermediate 44).

B. Preparation of the Final Compounds

EXAMPLE B1

A mixture of intermediate 9 (0.0106 mol), 1,1'-carbonyldiimidazole (0.0318 mol) and NaH (0.0001 mol) in THF (60 ml) was stirred at room temperature for 30 min. The mixture was poured into water and extracted with EtOAc. The organic layer was dried ($MgSO_4$), filtered off and evaporated till dryness. The residue was purified by column chromatography over silica gel (eluent: toluene/2-propanol/$NH_4OH$ 90/10/0.1) (15–40 µm). The pure fractions were collected and evaporated. The residue (2.1 g) was crystallized from 2-propanone/DIPE, yielding 1.2 g (46%) of (±)-6-[(4-chlorophenyl)-1H-imidazol-1-ylmethyl]-4-phenoxy-2(1H)-quinolinone, melting point 233.3° C.

EXAMPLE B2

A mixture of 1-methyl-1H-imidazole (0.0206 mol) in THF (35 ml) was cooled to −70° C. under $N_2$ flow. BuLi 1.6M (12.9 ml) was added dropwise. The mixture was stirred at −70° C. for 30 min. Chlorotriethyl-silane (0.0206 mol) was added. The mixture was allowed to warm to 10° C. and then cooled to −70° C. BuLi 1.6M (12.9 ml) was added dropwise. The mixture was stirred at −70° C. for 1 hour, then brought to −15° C., cooled to −70° C. and poured out under $N_2$ flow into a solution of intermediate 16 (0.00825 mol) in THF (18 ml). The mixture was stirred at −70° C. for 30 min, then hydrolyzed, extracted with EtOAc and decanted. The organic layer was dried ($MgSO_4$), filtered and the solvent was evaporated. The residue (9 g) was purified by column chromatography over silica gel (eluent: $CH_2Cl_2/CH_3OH/NH_4OH$ 98/2/0.1; 15–40 µm). The pure fractions were collected and their solvents were evaporated. The residue was crystallized from 2-propanone/$CH_3CN$/DIPE. The precipitate was filtered off and dried, yielding 1.9 g of 4-[2-(3-chlorophenyl)ethyl]-6-[(4-chlorophenyl)hydroxy(1-methyl-1H-imidazol-5-yl)methyl]-1-methyl-2(1H)-quinolinone, mp 190° C.

EXAMPLE B3 a) Thionyl chloride (30 ml) was cooled on an ice bath and then poured out cold on 4-[2-(3-chlorophenyl)ethyl]-6-[(4-chlorophenyl)hydroxy(1-methyl-1H-imidazol-5-yl)methyl]-1-methyl-2(1H)-quinolinone (see Example B2) (0.0025 mol). The mixture was stirred at 40° C. for 2 hours. The solvent was evaporated till dryness. The product was used without further purification, yielding 6-[chloro(4-chlorophenyl)(1-methyl-1H-imidazol-5-yl)methyl]-4-[2-(3-chlorophenyl)ethyl]-1-methyl-2(1H)-quinolinone hydrochloride.

b) $NH_3$/2-propanol saturated (80 ml) was added dropwise at 10° C. to a mixture of 6-[chloro(4-chlorophenyl)(1-methyl-1H-imidazol-5-yl)methyl]-4-[2-(3-chlorophenyl)ethyl]-1-methyl-2(1H)-quinolinone (see Example B3a) (0.017 mol) in THF (80 ml). The mixture was stirred at room temperature for 3 hours, hydrolyzed and extracted with DCM. The organic layer was separated, dried ($MgSO_4$), filtered and the solvent was evaporated till dryness. The residue (14 g) was purified by column chromatography over silica gel (eluent: cyclohexane/2-propanol/$NH_4OH$ 64/35/1 and 48/50/2; 15–35 µm). The desired fractions were collected and the solvent was evaporated, yielding 7.2 g of residue which was crystallized from $CH_3CN$. The precipitate was filtered off and dried. The residue (5.3 g) was purified by column chromatography (eluent: $CH_3OH$/($NH_4OAc$ 1% in $H_2O$) 80/20). The pure fractions were collected and the solvent was evaporated. The residue (3.8 g) was crystallized from $CH_3CN$. The precipitate was filtered off and dried, yielding 3.2 g (36%) of 6-[amino(4-chlorophenyl)(1-methyl-1H-imidazol-5-yl)methyl]-4-[2-(3-chlorophenyl)ethyl]-1-methyl-2(1H)-quinolinone, melting point 165° C.

EXAMPLE B4

A mixture of intermediate 26 (0.0155 mol), 2-phenyl-1H-imidazole (0.0233 mol) and $K_2CO_3$ (0.0465 mol) in acetonitrile (200 ml) was stirred and refluxed for 6 hours and then cooled. The solvent was evaporated till dryness. The residue was taken up in DCM. The organic layer was separated, washed with water, dried ($MgSO_4$), filtered and the solvent was evaporated. The residue (10.7 g) was purified by column chromatography over silica gel (eluent: $CH_2Cl_2/CH_3OH/NH_4OH$ 96/4/0.5; 15–40 µm). Two pure fractions (F1 and F2) were collected and their solvents were evaporated, yielding 1.35 g F1 (14%) of 4-(3-chlorophenoxy)-6-[(4-chlorophenyl)(2-phenyl-1H-imidazol-1-yl)methyl]-1,2-dihydro-2-oxo-3-quinolinecarboxylic acid, ethyl ester and 0.8 g (8%) of F2. F2 was crystallized from 2-propanone and diethyl ether. The precipitate was filtered off and dried, yielding 0.65 g (7%) of 4-(3-chlorophenoxy)-6-[(4-chlorophenyl)(2-phenyl-1H-imidazol-5-yl)methyl]-1,2-dihydro-2-oxo-3-quinolinecarboxylic acid ethyl ester, melting point 189° C.

EXAMPLE B5

A solution of 4-(3-chlorophenoxy)-6-[(4-chlorophenyl)(2-phenyl-1H-imidazol-1-yl)methyl]-1,2-dihydro-2-oxo-3-quinolinecarboxylic acid, ethyl ester (see Example B4) (0.00221 mol) in THF (12 ml) was added dropwise at 5° C. under $N_2$ flow to a mixture of $LiAlH_4$ (0.00443 mol) in THF (10 ml). The mixture was stirred at 5° C. for 1 hour, brought to room temperature, stirred at room temperature for 2 hours and then cooled. EtOAc was added dropwise. The mixture was hydrolyzed slowly, filtered over celite and washed with EtOAc. The filtrate was extracted with EtOAc. The organic layer was separated, washed with water, dried ($MgSO_4$), filtered and the solvent was evaporated. The residue (1.25 g) was purified by column chromatography over silica gel (eluent: $CH_2Cl_2/CH_3OH/NH_4OH$ 97/3/0.1; 15–40 µm). The pure fractions were collected and the solvent was evaporated. The residue was crystallized from 2-propanone and diethyl ether. The precipitate was filtered off and dried, yielding 0.72 g (57%) of 4-(3-chlorophenoxy)-6-[(4-chlorophenyl)(2-phenyl-1H-imidazol-1-yl)methyl]-3-(hydroxymethyl)-2(1H)-quinolinone, melting point 246° C.

EXAMPLE B6

Sodium azide (0.0123 mol) was added to a mixture of intermediate 30 (0.0041 mol) in DMF (50 ml). The mixture was stirred at 140° C. for 5 hours and poured out into water. The precipitate was filtered off and taken up in DCM. The organic solution was dried ($MgSO_4$), filtered and the solvent was evaporated till dryness. The residue (2.2 g) was purified by column chromatography over silica gel (eluent: toluene/2-propanol/$NH_4OH$ 90/10/0.6; 15–40 µm). The pure fractions were collected and the solvent was evaporated. The residue was crystallized from 2-propanone and $CH_3CN$. The precipitate was filtered off and dried, yielding 1 g (46%) of α-(4-chlorophenyl)-5-[2-(3-chlorophenyl)ethyl]-α-(1-methyl-1H-imidazol-5-yl)-tetrazolo[1,5-α]quinoline-7-methanol, melting point 242° C.

EXAMPLE B7 a) A mixture of α-(4-chlorophenyl)-5-[2-(3-chlorophenyl)ethyl]-α-(1-methyl-1H-imidazol-5-yl)-tetrazolo[1,5-α]quinoline-7-methanol (see Example B6) (0.00302 mol) in thionyl chloride (15 ml) was stirred at room temperature for 4 hours. The solvent was evaporated till dryness. The product was used without further purification, yielding 7-[chloro(4-chlorophenyl)(1-methyl-1H-imidazol-5-yl)methyl]-5-[2-(3-chlorophenyl)ethyl]-tetrazolo[1,5-α]quinoline hydrochloride (1:1)

b) 2-propanol/NH$_3$ saturated (10 ml) was added dropwise at 0° C. to a mixture of 7-[chloro(4-chlorophenyl)(1-methyl-1H-imidazol-5-yl)methyl]-5-[2-(3-chlorophenyl)ethyl]-tetrazolo[1,5-α]quinoline hydrochloride (1:1) (see Example B7a) (0.00302 mol) in THF (20 ml). The mixture was stirred at 0° C. for 30 min, hydrolized and extracted with DCM. The organic layer was separated, dried (MgSO$_4$), filtered and the solvent was evaporated till dryness. The residue (1.65 g) was purified by column chromatography over silica gel (eluent: toluene/2-propanol/NH$_4$OH 90/10/0.2; 15–40 μm). The pure fractions were collected and the solvent was evaporated. The residue was dissolved in CH$_3$CN and converted into the ethanedioic acid salt (1:2). The precipitate was filtered off and dried, yielding 0.18 g (8.2%) of α-(4-chlorophenyl)-5-[2-(3-chlorophenyl)ethyl]-α-(1-methyl-1H-imidazol-5-yl)-tetrazolo[1,5-α]quinoline-7-methanamine, melting point 160° C.

EXAMPLE B8

A mixture of intermediate 35 (0.0047 mol) and sodium azide (0.0141 mol) in DMF (25 ml) was stirred at 140° C. for 3 hours and poured out into ice water. The precipitate was filtered off, washed with water and taken up in DCM. The organic layer was separated, dried (MgSO$_4$), filtered and the solvent was evaporated till dryness. The residue was crystallized from 2-propanone and DIPE. The precipitate was filtered off and dried, yielding 2 g (86%) of α-(4-chlorophenyl)-α-(1-methyl-1H-imidazol-5-yl)-5-(2-phenylethyl)-tetrazolo[1,5-α]quinoline-7-methanol, melting point 247° C.

EXAMPLE B9

Sulfuric acid concentrated (0.8 ml) was added to a mixture of α-(4-chlorophenyl)-5-[2-(3-chlorophenyl)ethyl]-α-(1-methyl-1H-imidazol-5-yl)-tetrazolo[1,5-α]quinoline-7-methanol (see Example B6) (0.0019 mol) in acetonitrile (10 ml). The mixture was stirred at 80° C. for 3 hours, then poured out into K$_2$CO$_3$ 10% and extracted with DCM. The organic layer was separated, dried (MgSO$_4$), filtered and the solvent was evaporated till dryness. The residue was crystallized from diethyl ether. The precipitate was filtered off and dried, yielding 0.51 g (47%) of N-[(4-chlorophenyl)[5-[2-(3-chlorophenyl)ethyl]tetrazolo[1,5-α]quinolin-7-yl](1-methyl-1H-imidazol-5-yl)methyl]-acetamide, melting point 200° C.

EXAMPLE B10

Sulfuric acid concentrated (0.5 ml) was added to a mixture of α-(4-chlorophenyl)-α-(1-methyl-1H-imidazol-5-yl)-5-(2-phenylethyl)-tetrazolo[1,5-α]quinoline-7-methanol (see Example B8) (0.00202 mol) in acetonitrile (10 ml). The mixture was stirred and refluxed for 2 hours, poured out on ice and a concentrated NH$_4$OH solution and extracted with EtOAc. The mixture was stirred for 30 min. The organic layer was separated, dried (MgSO$_4$), filtered and the solvent was evaporated till dryness. The residue was crystallized from diethyl ether. The precipitate was filtered off and dried, yielding 0.45 g (42%) of N-[(4-chlorophenyl)(1-methyl-1H-imidazol-5-yl)[5-(2-phenylethyl)tetrazolo[1,5-α]quinolin-7-yl]methyl]-acetamide, melting point 170° C.

EXAMPLE B11

BuLi 1.6M (1.6 ml, 0.0025 mol) was added dropwise at −70° C. to a solution of 1-methyl-1H-imidazole (0.0025 mol) in THF (5 ml) under N$_2$ flow. The mixture was stirred for 10 minutes. ClSiEt$_3$ (0.0026 mol) was added. The mixture was stirred for 10 minutes. BuLi 1.6M (1.4 ml, 0.0022 mol) was added. The mixture was stirred for 15 minutes. A solution of intermediate 42 (0.00143 mol) in THF (15 ml) was added. The mixture was stirred at −70° C. for 1 hours and 30 minutes, poured out into NH$_4$Cl 10% and extracted with EtOAc. The organic layer was separated, dried (MgSO$_4$), filtered and the solvent was evaporated. The residue (1.15 g) was purified by column chromatography over silica gel (eluent: CH$_2$Cl$_2$/CH$_3$OH/NH$_4$OH 94/6/0.1; 15–40 μm). The pure fractions were collected and the solvent was evaporated. The residue (0.3 g) was crystallized from 2-propanone. The precipitate was filtered off and dried, yielding 0.21 g (27%) of N-(3-chlorophenyl)-6-[(4-chlorophenyl)hydroxy(1-methyl-1H-imidazol-5-yl)methyl]-1,2-dihydro-N,1-dimethyl-2-oxo-4-quinolinecarboxamide, melting point 218° C.

EXAMPLE B12

BuLi (4.4 ml, 0.0071 mol) was added dropwise at −70° C. to a solution of 1-methyl-1H-imidazole (0.0071 mol) in THF (15 ml) under N$_2$ flow. The mixture was stirred for 10 minutes. Chlorotriethyl-silane (0.0073 mol) was added. The mixture was stirred for 10 minutes. BuLi (3.9 ml, 0.0063 mol) was added. The mixture was stirred for 10 minutes. A solution of intermediate 44 (0.004 mol) in THF (20 ml) was added. The mixture was stirred at −70° C. for 1 hour and 30 minutes, poured out into NH$_4$Cl 10% and extracted with EtOAc. The organic layer was separated, dried (MgSO$_4$), filtered, and the solvent was evaporated. The residue (3.8 g) was purified by column chromatography over silica gel (eluent: CH$_2$Cl$_2$/CH$_3$OH/NH$_4$OH 94/6/0.5; 15–40 μm). The pure fractions were collected and the solvent was evaporated, yielding 1.1 g of a residue which was crystallized from petroleum ether. The precipitate was filtered off and dried, yielding 0.92 g (43%) of 6-[(4-chlorophenyl)hydroxy(1-methyl-1H-imidazol-5-yl)methyl]-1,2-dihydro-N,1-dimethyl-N-(3-methylphenyl)-2-oxo-4-quinolinecarboxamide, melting point 185° C.

EXAMPLE B13

2,2,2-Trichloroethyl-carbonochloridic acid ester (0.0072 mol) was added at room temperature to a mixture of 6-[amino(4-chlorophenyl)(1-methyl-1H-imidazol-5-yl)methyl]-4-[2-(3-chlorophenyl)ethyl]-1-methyl-2(1H)-quinolinone, obtained in Example B3 (0.0014 mol) in DMF (10 ml). The mixture was stirred for 1 hour, poured out into ice water, basified with K$_2$CO$_3$ and extracted with EtOAc. The organic layer was separated, dried (MgSO$_4$), filtered, and the solvent was evaporated. The residue was crystallized from CH$_3$CN/DIPE. The precipitate was filtered off and dried, yielding 0.54 g (65%) of N'-[(Z)-(4-chlorophenyl)[4-[2-(3-chlorophenyl)ethyl]-1,2-dihydro-1-methyl-2-oxo-6-quinolinyl](1-methyl-1H-imidazol-5-yl)methyl]-N,N-dimethyl-methanimidamide (E), melting point 198° C.

EXAMPLE B14

BuLi (0.0105 mol) was added dropwise at –70° C. to a mixture of 3-bromo-pyridine (0.0105 mol) in diethyl ether (15 ml) under $N_2$ flow. The mixture was stirred at –70° C. for 15 minutes. A solution of intermediate 16 (0.0053 mol) in THF (25 ml) was added at –70° C. The mixture was stirred at –70° C. for 30 minutes, poured out into ice water and extracted with EtOAc. The organic layer was separated, dried ($MgSO_4$), filtered and the solvent was evaporated. The residue was purified by column chromatography over silica gel (eluent: $CH_2Cl_2/CH_3OH/NH_4OH$ 99/1/0.1; 15–40 μm). The pure fractions were collected and the solvent was evaporated, yielding 1.5 g (55%) of 4-[2-(3-chlorophenyl)ethyl]-6-[(4-chlorophenyl)hydroxy-3-pyridinylmethyl]-1-methyl-2(1H)-quinolinone, melting point 115° C.

EXAMPLE B15 a) A mixture of 4-[2-(3-chlorophenyl)ethyl]-6-[(4-chlorophenyl)hydroxy-3-pyridinylmethyl]-1-methyl-2(1H)-quinolinone, obtained in Example B14 (0.0026 mol) in $SOCl_2$ (15 ml) was stirred at room temperature for 3 hours. The solvent was evaporated till dryness. The residue was taken up in DCM. The solvent was evaporated, yielding 1.5 g of 6-[chloro(4-chlorophenyl)-3-pyridinylmethyl]-4-[2-(3-chlorophenyl)ethyl]-1-methyl-2(1H)-quinolinone hydrochloride (1:1). This fraction was used directly in the next reaction step.

b) $NH_3/iPrOH$ (20 ml) was added dropwise at 10° C. to a mixture of 6-[chloro(4-chlorophenyl)-3-pyridinylmethyl]-4-[2-(3-chlorophenyl)ethyl]-1-methyl-2(1H)-quinolinone (0.0026 mol) in THF (15 ml). The mixture was brought to room temperature, stirred for 2 hours, poured out into ice water and extracted with EtOAc. The organic layer was separated, dried ($MgSO_4$), filtered, and the solvent was evaporated. The residue (1.5 g) was purified by column chromatography over silica gel (eluent: $CH_2Cl_2/CH_3OH/NH_4OH$ 96/4/0.2; 15–40 μm). The pure fractions were collected and the solvent was evaporated, yielding 0.65 g (48%) of 6-[amino(4-chlorophenyl)-3-pyridinylmethyl]-4-[2-(3-chlorophenyl)ethyl]-1-methyl-2(1H)-quinolinone, melting point 90° C.

EXAMPLE B16

2,2,2-trichloroethyl carbonochloridic acid ester (0.00724 mol) was added to a solution of 6-[amino(4-chlorophenyl)(1-methyl-1H-imidazol-5-yl)methyl]-4-[2-(3-chlorophenyl)ethyl]-1-methyl-2(1H)-quinolinone (R121550), obtained in Example B3 (0.00145 mol) in THF (10 ml). The mixture was stirred at 80° C. for 2 hours and poured out into ice water. AcOEt was added and the mixture was basified with potassium carbonate. The organic layer was separated, dried ($MgSO_4$), filtered, and the solvent was evaporated. The residue (1.6 g) was purified by column chromatography over silica gel (eluent: $CH_2Cl_2/CH_3OH/NH_4OH/96/4/0.2$; 15–40 μm). The pure fractions were collected and the solvent was evaporated, yielding 0.32 g of a residue which was further purified by column chromatography over silica gel (eluent: toluene/2-propanol/90/10; kromasyl 5 μm). yielding 0.139 g (14%) of [(4-chlorophenyl)[4-[2-(3-chlorophenyl)ethyl]-1,2-dihydro-1-methyl-2-oxo-6-quinolinyl](1-methyl-1H-imidazol-5-yl)methyl]-carbamic acid, 2,2,2-trichloroethyl ester, MS ($MH^+$) m/e: 691, 693, 695, 697, 699.

EXAMPLE B17

$H_2SO_4$ concentrated (3 drops) was added to a mixture of α-(4-chlorophenyl)-5-[2-(3-chlorophenyl)ethyl]-α-(1-methyl-1H-imidazol-5-yl)-tetrazolo[1,5-α]quinoline-7-methanol, obtained in Example B6 (0.0013 mol) in 1,2-ethanediol (7 ml). The mixture was stirred at 125° C. for 18 hours, then poured out into ice/$K_2CO_3$ 10% and extracted with DCM. The organic layer was separated, dried ($MgSO_4$), filtered, and the solvent was evaporated till dryness. The residue (0.88 g) was purified by column chromatography over silica gel (eluent: toluene/iPrOH/$NH_4OH$ 85/15/1; 15–40 μm). The pure fractions were collected and the solvent was evaporated. The residue (0.4 g, 54%) was crystallized from $CH_3CN$. The precipitate was filtered off and dried, yielding 0.32 g (43%) of 2-[(4-chlorophenyl)[5-[2-(3-chlorophenyl)ethyl]tetrazolo[1,5-α]quinazolin-7-yl](1-methyl-1H-imidazol-5-yl)methoxy]-ethanol, melting point 229° C.

EXAMPLE B18

$H_2SO_4$ (3 drops) was added to a mixture of α-(4-chlorophenyl)-5-[2-(3-chlorophenyl)ethyl]α-(1-methyl-1H-imidazol-5-yl)-tetrazolo[1,5-α]quinoline-7-methanol, obtained in Example B6 (0.0013 mol) in 2-methoxy-ethanol (7 ml). The mixture was stirred at 125° C. for 48 hours, poured out into ice/$K_2CO_3$ 10% and extracted with DCM. The organic layer was separated, dried ($MgSO_4$), filtered, and the solvent was evaporated till dryness. The residue was purified by column chromatography over silica gel (eluent: $CH_2Cl_2/CH_3OH/NH_4OH$ 97.5/2.5/0.1; 15–40 μm). The pure fractions were collected and the solvent was evaporated. The residue (0.12 g, 16%) was dissolved in 2-propanone/DIPE and converted into the ethanedioic acid salt. The precipitate was filtered off and dried, yielding 0.1 g (11%) of 5-[2-(3-chlorophenyl)ethyl]-7-[(4-chlorophenyl)(2-methoxyethoxy)(1-methyl-1H-imidazol-5-yl)methyl]-tetrazolo[1,5-α]quinoline ethanedioate (1:1) hydrate (1:1), melting point 156° C.

EXAMPLE B19

BuLi 1.6M in hexane (0.014 mol) was added dropwise at –70° C. to a mixture of 2,4-dihydro-4-methyl-3H-1,2,4-triazole-3-thione (0.0074 mol) in THF (40 ml) under $N_2$ flow. The mixture was stirred at –70° C. for 30 minutes, then brought to 0° C., stirred for 30 minutes and cooled again to –70° C. Intermediate 16 (0.0038 mol) was added portionwise. The mixture was stirred for 30 minutes, then brought to 0° C., stirred at room temperature for a week-end, poured out into water and extracted with EtOAc. The organic layer was separated, dried ($MgSO_4$), filtered, and the solvent was evaporated. The residue was purified by column chromatography over silica gel (eluent: $CH_2Cl_2/CH_3OH/NH_4OH$ 95/5/0.2; 15–40 μm). The pure fractions were collected and the solvent was evaporated, yielding 0.22 g (10%) of 4-[2-(3-chlorophenyl)ethyl]-6-[(4-chlorophenyl)hydroxy(5-mercapto-4-methyl-4H-1,2,4-triazol-3-yl)methyl]-1-methyl-2(1H)-quinolinone, MS ($MH^+$) m/e: 551, 553, 555.

EXAMPLE B20

Sodium nitrite (0.0007 mol) was added at 0° C. to a mixture of nitric acid (0.0007 mol) in water (1 ml). A solution of 4-[2-(3-chlorophenyl)ethyl]-6-[(4-chlorophenyl)hydroxy(5-mercapto-4-methyl-4H-1,2,4-triazol-3-yl)methyl]-1-methyl-2(1H)-quinolinone, obtained in Example B19 (0.0007 mol) in THF (3 ml) was added dropwise (very exothermic reaction). The mixture was stirred at room temperature for 30 minutes, poured out into ice water and extracted with DCM. The organic layer was separated, washed with K$_2$CO$_3$ 10%, dried (MgSO$_4$), filtered and the solvent was evaporated. The residue was purified by column chromatography over kromasyl (eluent: CH$_2$Cl$_2$/CH$_3$OH/ NH$_4$OH 96/4/0.4; 5 μm). The pure fractions were collected and the solvent was evaporated. The residue (0.25 g) was crystallized from CH$_3$CN. The precipitate was filtered off and dried, yielding 0.12 g (32%) of 4-[2-(3-chlorophenyl) ethyl]-6-[(4-chlorophenyl)hydroxy(4-methyl-4H-1,2,4-triazol-3-yl)methyl]-1-methyl-2(1H)-quinolinone, melting point 200° C.

The following compounds were prepared analogous to the one of the above examples (the example number analogous to which they were prepared is indicated between square brackets after the compound number).

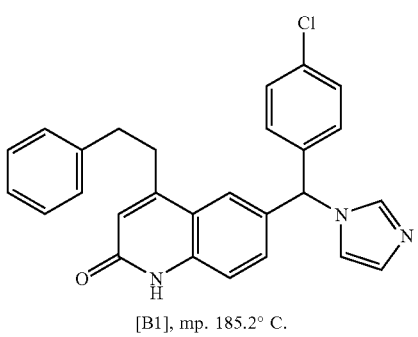

[B1], mp. 185.2° C.

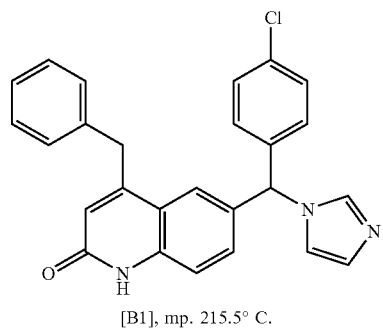

[B1], mp. 215.5° C.

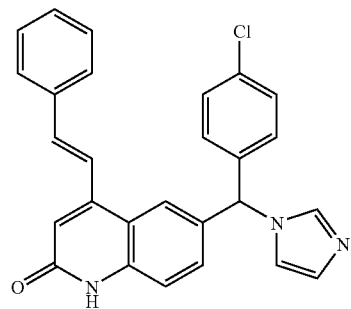

[B1], mp. 162.4° C.

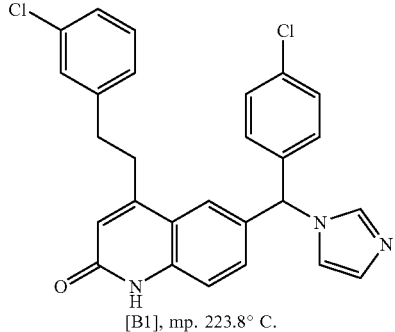

[B1], mp. 223.8° C.

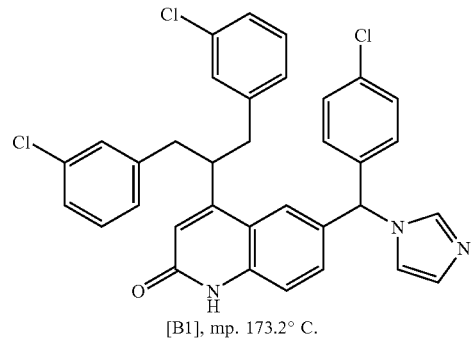

[B1], mp. 173.2° C.

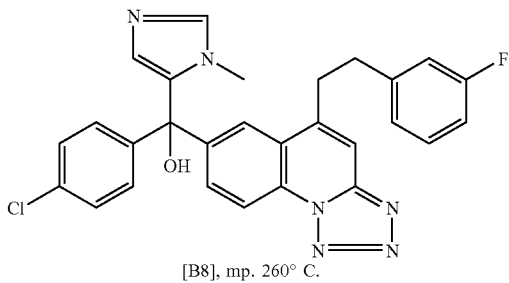

[B8], mp. 260° C.

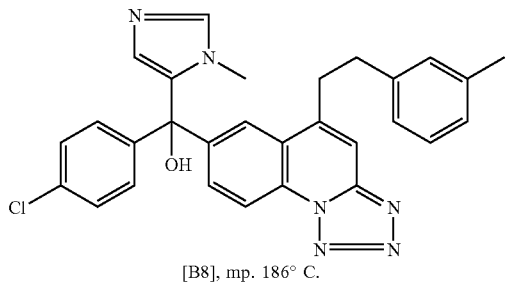

[B8], mp. 186° C.

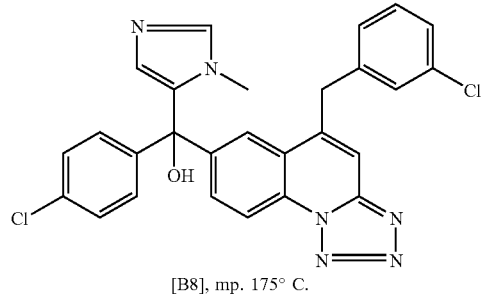

[B8], mp. 175° C.

-continued

[B9], mp. 230° C.

[B8], mp. 230° C.

C. Pharmacological Example.

EXAMPLE C1

"In Vitro Assay for Inhibition of Farnesyl Protein Transferase"

An in vitro assay for inhibition of farnesyl transferase was performed essentially as described in WO 98/40383, pages 33–34.

EXAMPLE C2

"Ras-Transformed Cell Phenotype Reversion Assay"

The ras-transformed cell phenotype reversion assay was performed essentially as described in WO 98/40383, pages 34–36.

EXAMPLE C3

"Farnesyl Protein Transferase Inhibitor Secondary Tumor Model"

The farnesyl protein transferase inhibitor secondary tumor model was used as described in WO 98/40383, page 37.

D. Composition Example: Film-coated Tablets

Preparation of Tablet Core

A mixture of 100 g of a compound of formula (I), 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A compound of formula (I):

(I)

or a pharmaceutically acceptable salt or N-oxide or stereochemically isomeric form thereof, wherein:

r and s are each independently 0, 1, 2, 3, 4 or 5;

t is 0, 1, 2 or 3;

>$Y^1$—$Y^2$— is a trivalent radical of formula

>C=N— (y-1)

>C=$CR^9$— (y-2)

>CH—$NR^9$— (y-3)

>CH—$CHR^9$— (y-4)

wherein $R^9$ is hydrogen, halo, cyano, $C_{1-6}$alkyl, hydroxy$C_{1-6}$alkyl, $C_{1-6}$alkyloxy$C_{1-6}$alkyl, —$(CR^{20}R^{21})_p$—$C_{3-10}$cycloalkyl, $C_{2-6}$alkenyl, $C_{2-6}$alkynyl, halocarbonyl, hydroxycarbonyl, $C_{1-6}$alkyloxycarbonyl, aryl or a group of formula —$C_{1-6}$alkyl-$NR^{22}R^{23}$, —$C_{2-6}$alkenyl-$NR^{22}R^{23}$, —$CONR^{22}R^{23}$ or —$NR^{22}$—$C_{1-6}$alkyl-$NR^{22}R^{23}$;

Z is —O—, —S—, —SO—, —$SO_2$—, —$NR^{22}$—, -Alk-, $C_{2-4}$alkenediyl, —O-Alk-, -Alk-O—, —$S(O)_{0-2}$-Alk-, -Alk-$S(O)_{0-2}$, —OC(O)-Alk-, -Alk —OC(O)—, —$NR^{22}$-Alk-, -Alk-$NR^{22}$—, —$NR^{22}$— C(O)— or —C(O) —$NR^{22}$— (wherein Alk is $C_{1-6}$alkanediyl) and wherein the Alk or alkenediyl moiety may be optionally substituted by one or more substituents independently selected from $C_{1-6}$alkyl, $C_{1-6}$alkyloxy, aryl$C_{1-6}$alkyl or $Ar^2$, and where necessary to establish the configuration of any Z group, the first atom recited above in any such group being that which is linked to the $Y^1$ grouping in formula (I);

each $R^1$ and $R^2$ is independently azido, hydroxy, halo, cyano, nitro, $C_{1-6}$alkyl, —$(CR^{20}R^{21})_p$—$C_{3-10}$cycloalkyl, cyano$C_{1-6}$alkyl, hydroxy$C_{1-6}$alkyl, $C_{1-6}$alkyloxy$C_{1-6}$alkyl, hydroxycarbonyl$C_{1-6}$alkyloxy$C_{1-6}$alkyl, $R^{24}SC_{1-6}$alkyl, trihalomethyl, aryl$C_{1-6}$alkyl, Het$^2C_{1-6}$alkyl, —$C_{1-6}$alkyl-$NR^{22}R^{23}$, —$C_{1-6}$alkyl$NR^{22}C_{1-6}$alkyl-$NR^{22}R^{23}$, —$C_{1-6}$alkyl$NR^{22}$-Het$^2$, —$C_{1-6}$alkyl$NR^{22}$—$C_{1-6}$alkyloxy$C_{1-6}$alkyl, —$C_{1-6}$akyl$NR^{22}$—$C_{1-6}$ alkyl-S—$C_{1-6}$alkyl-Ar$^2$, —$C_{1-6}$alkyl$NR^{22}$—$C_{1-6}$ alkyl-S—$C_{1-6}$alkyl, —$C_{1-6}$alkyl$NR^{22}C_{1-6}$alkyl-Ar$^2$ (wherein the $C_{1-6}$alkyl moiety adjacent to the Ar$^2$ is optionally substituted by $C_{1-6}$alkyloxycarbonyl), —$C_{1-6}$ alkyl$NR^{22}C_{1-6}$alkyl-Het$^2$, —$C_{1-6}$ alkyl$NR^{22}COC_{1-6}$ alkyl, —$C_{1-6}$alkyl$NR^{22}$COAlkAr$^2$, —$C_{1-6}$ alkyl$NR^{22}$COAr$^2$, $C_{1-6}$alkylsulphonylamino$C_{1-6}$ alkyl, $C_{1-6}$alkyloxy, hydroxy$C_{1-6}$alkyloxy, $C_{1-6}$alkyloxy$C_{1-6}$ alkyloxy, —$OC_{1-6}$alkyl-$NR^{22}R^{23}$, trihalomethoxy, aryl$C_{1-6}$alkyloxy, Het$^2C_{1-6}$alkyloxy, $C_{1-6}$alkylthio, $C_{2-6}$alkenyl, cyano$C_{2-6}$alkenyl, —$C_{2-6}$alkenyl-$NR^{22}R^{23}$, hydroxycarbonyl$C_{2-6}$alkenyl, $C_{1-6}$alkyloxycarbonyl$C_{2-6}$alkenyl, $C_{2-6}$alkynyl, —CHO, $C_{1-6}$alkylcarbonyl, hydroxy$C_{1-6}$alkylcarbonyl, hydroxycarbonyl, $C_{1-6}$alkyloxycarbonyl, —$CONR^{22}R^{23}$, —$CONR^{22}$—$C_{1-6}$alkyl-$NR^{22}R^{23}$, —$CONR^{22}$—$C_{1-6}$alkyl-Het$^2$, —$CONR^{22}$—$C_{1-6}$alkyl-Ar$^2$, —$CONR^{22}$-Het$^2$, —$CONR^{22}Ar^2$, —$CONR^{22}$—O—$C_{1-6}$alkyl, —$CONR^{22}$—$C_{1-6}$alkenyl, —$NR^{22}R^{23}$, —$OC(O)R^{24}$, —$CR^{24}$=$NR^{25}$, —$CR^{24}$=N—$OR^{25}$, —$NR^{24}C(O)$ $NR^{22}R^{23}$, —$NR^{24}SO_2R^{25}$, —$NR^{24}C(O)R^{25}$, —$S(O)_{0-2}R^{24}$, —$SO_2NR^{24}R^{25}$, —$C(NR^{26}R^{27})$=$NR^{28}$ —$Sn(R^{24})_3$, —$SiR^{24}R^{24}R^{25}$, —$B(OR^{24})_2$, —$P(O)OR^{24}OR^{25}$, Ar$^2$oxy, Het$^2$-oxy, or a group of formula -Z, —CO-Z or —CO—$NR^y$-Z
in which $R^y$ is hydrogen or $C_{1-4}$alkyl and Z is phenyl or a 5- or 6-membered heterocyclic ring containing one or more heteroatoms selected from oxygen, sulphur and nitrogen, the phenyl or heterocyclic ring being optionally substituted by one or two substituents each independently selected from halo, cyano, —$COOR^{24}$, aminocarbonyl, $C_{1-6}$alkylthio, hydroxy, —$NR^{22}R^{23}$, $C_{1-6}$alkylsulphonylamino, $C_{1-6}$alkyl, halo$C_{1-6}$alkyl, $C_{1-6}$alkyloxy or phenyl; or
two $R^1$ or $R^2$ substituents adjacent to one another on the phenyl ring may form together a bivalent radical of formula —O—CH$_2$—O— (a-1)

—O—CH$_2$—CH$_2$—O— (a-2)

—O—CH=CH— (a-3)

—O—CH$_2$—CH$_2$— (a-4)

—O—CH$_2$—CH$_2$—CH$_2$— (a-5)

—CH=CH—CH=CH— (a-6)

p is 0 to 5;
$R^{20}$ and $R^{21}$ are independently hydrogen or $C_{1-6}$ alkyl and are independently defined for each iteration of p in excess of 1;
$R^{22}$ and $R^{23}$ are independently hydrogen, $C_{1-6}$ alkyl or —$(CR^{20}R^{21})_p$—$C_{3-10}$cycloalkyl, or together with the adjacent nitrogen atom form a 5- or 6-membered heterocyclic ring optionally containing one, two or three further heteroatoms selected from oxygen, nitrogen or sulphur and optionally substituted by one or two substituents each independently selected from halo, hydroxy, cyano, nitro, $C_{1-6}$alkyl, halo$C_{1-6}$alkyl, $C_{1-6}$alkyloxy, OCF$_3$, hydroxycarbonyl, $C_{1-6}$alkyloxycarbonyl, aminocarbonyl, mono- or di-($C_{1-6}$alkyl)aminocarbonyl, amino, mono- or di-($C_{1-6}$alkyl)amino, $C_{1-6}$alkylsulfonylamino, oxime, or phenyl;
$R^{24}$ and $R^{25}$ are independently hydrogen, $C_{1-6}$ alkyl, —$(CR_{20}R_{21})_p$—$C_{3-10}$cycloalkyl or aryl$C_{1-6}$alkyl;
$R^{26}$, $R^{27}$ and $R^{28}$ are independently hydrogen and $C_{1-6}$alkyl or —$C(O)C_{1-6}$alkyl;
$R^3$ is hydrogen, halo, cyano, $C_{1-6}$alkyl, —$(CR^{20}R^{21})_p$—$C_{3-10}$cycloalkyl, halo$C_{1-6}$alkyl, cyano$C_{1-6}$alkyl, hydroxy$C_{1-6}$alkyl, $C_{1-6}$alkyloxy$C_{1-6}$alkyl, aryl$C_{1-6}$alkyloxy$C_{1-6}$alkyl, $C_{1-6}$alkylthio$C_{1-6}$alkyl, hydroxycarbonyl$C_{1-6}$alkyl, $C_{1-6}$alkylcarbonyl$C_{1-6}$alkyl, $C_{1-6}$alkyloxycarbonyl$C_{1-6}$alkyl, —$C_{1-6}$alkyl-$NR^{22}R^{23}$, —$C_{1-6}$alkyl-$CONR^{22}R^{23}$, aryl$C_{1-6}$alkyl, Het$^2C_{1-6}$alkyl, $C_{2-6}$alkenyl, —$C_{2-6}$alkenyl $NR^{22}R^{23}$, $C_{2-6}$alkynyl, hydroxycarbonyl, $C_{1-6}$alkyloxycarbonyl, aryl, or Het$^2$; or a radical of formula —O—$R^{10}$ (b-1)

—S—$R^{10}$ (b-2)

—$NR^{11}R^{12}$ (b-3)

—N=$CR^{10}R^{11}$ (b-4)

wherein
$R^{10}$ is hydrogen, $C_{1-6}$alkyl, —$(CR^{20}R^{21})_p$—$C_{3-10}$cycloalkyl, aryl$C_{1-6}$alkyl, $C_{2-6}$alkenyl, $C_{2-6}$alkynyl, $C_{1-6}$alkylcarbonyl, aryl, a group of formula —$NR^{22}R^{23}$ or —$C_{1-6}$alkylC(O)OC$_{1-6}$alkyl $NR^{22}R^{23}$, or a radical of formula -Alk-OR$^{13}$ or -Alk-$NR^{14}R^{15}$;
$R^{11}$ is hydrogen, $C_{1-6}$alkyl, —$(CR^{20}R^{21})_p$—$C_{3-10}$cycloalkyl, $C_{2-6}$alkenyl, $C_{2-6}$alkynyl, aryl or aryl$C_{1-6}$ alkyl;
$R^{12}$ is hydrogen, hydroxy, $C_{1-6}$alkyl, —$(CR^{20}R^{21})_p$—$C_{3-10}$cycloalkyl, $C_{1-6}$alkylcarbonyl$C_{1-6}$alkyl, aryl$C_{1-6}$ alkyl, $C_{2-6}$alkenyl, $C_{2-6}$alkynyl, aryl, $C_{1-6}$alkyloxy, a group of formula —$NR^{22}R^{23}$, $C_{1-6}$alkylcarbonylamino, $C_{1-6}$alkylcarbonyl, halo$C_{1-6}$ alkylcarbonyl, aryl$C_{1-6}$alkylcarbonyl, Het$^2C_{1-6}$ alkylcarbonyl, arylcarbonyl, $C_{1-6}$alkyloxycarbonyl, trihalo$C_{1-6}$alkyloxycarbonyl, $C_{1-6}$alkyloxy$C_{1-6}$alkylcarbonyl, aminocarbonyl, mono- or di-($C_{1-6}$alkyl)aminocarbonyl (wherein the alkyl moiety may optionally be substituted by one or more substituents independently selected from aryl and $C_{1-6}$alkyloxycarbonyl substituents) aminocarbonylcarbonyl, mono- or di-($C_{1-6}$alkyl)amino$C_{1-6}$alkylcarbonyl, or a radical of formula -Alk-OR$^{13}$ or -Alk-$NR^{14}R^{15}$;
$R^{13}$ is hydrogen, $C_{1-6}$alkyl, —$(CR^{20}R^{21})$—$C_{3-10}$cycloalkyl, $C_{2-6}$alkenyl, $C_{2-6}$alkynyl, $C_{1-6}$alkylcarbonyl, hydroxy$C_{1-6}$alkyl, aryl or aryl$C_{1-6}$alkyl;
$R^{14}$ is hydrogen, $C_{1-6}$alkyl, —$(CR^{20}R^{21})_p$—$C_{3-10}$cycloalkyl, $C_{2-6}$alkenyl, $C_{2-6}$alkynyl, aryl or aryl$C_{1-6}$alkyl;
$R^{15}$ is hydrogen, $C_{1-6}$alkyl, —$(CR^{20}R^{21})_p$—$C_{3-10}$cycloalkyl, $C_{2-6}$alkenyl, $C_{2-6}$alkynyl, $C_{1-6}$alkylcarbonyl, aryl or aryl$C_{1-6}$alkyl;
$R^4$ is a radical of formula

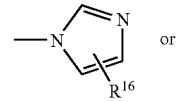

(c-1)

-continued

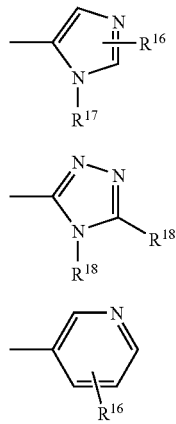

(c-2)

(c-3)

(c-4)

wherein

R$^{16}$ is hydrogen, halo, C$_{1-6}$alkyl, —(CR$^{20}$R$^{21}$)$_p$—C$_{3-10}$cycloalkyl, hydroxyC$_{1-6}$alkyl, C$_{1-6}$alkyloxyC$_{1-6}$alkyl, C$_{1-6}$alkylS(O)$_{0-2}$C$_{1-6}$alkyl, C$_{1-6}$alkyloxy, C$_{1-6}$alkylthio, a group of formula —NR$^{22}$R$^{23}$, —NHCOC$_{1-6}$alkyl, hydroxycarbonyl, C$_{1-6}$alkyloxycarbonyl or aryl, R$^{17}$ is hydrogen, C$_{1-6}$alkyl, —(CR$^{20}$R$^{21}$)$_p$—C$_{3-10}$cycloalkyl, hydroxyC$_{1-6}$alkyl, C$_{1-6}$alkyloxyC$_{1-6}$alkyl, aryl C$_{1-6}$alkyl, trifluoromethyl, trifluoromethylC$_{1-6}$alkyl, hydroxycarbonylC$_{1-6}$alkyl, C$_{1-6}$alkyloxycarbonylC$_{1-6}$alkyl, mono- or di-(C$_{1-6}$alkyl)aminosulphonyl or —C$_{1-6}$alkyl P(O)OR$^{24}$OR$^{25}$;

R$^{18}$ is hydrogen, C$_{1-6}$alkyl, —(CR$^{20}$R$^{21}$)$_p$—C$_{3-10}$cycloalkyl, arylC$_{1-6}$alkyl or C$_{1-6}$alkyloxyC$_{1-6}$alkyl;

R$^{18a}$ is hydrogen, —SH or —SC$_{1-4}$alkyl;

R$^5$ is cyano, hydroxy, halo, C$_{1-6}$alkyl, —(CR$^{20}$R$^{21}$)$_p$—C$_{3-10}$cycloalkyl, C$_{2-6}$alkenyl, C$_{2-6}$alkynyl, C$_{1-6}$alkyloxy, arylC$_{1-6}$alkyloxy, Het$^2$C$_{1-6}$alkyloxy, hydroxycarbonyl, C$_{1-6}$alkyloxycarbonyl, or a group of formula —NR$^{22}$R$^{23}$ or —CONR$^{22}$R$^{23}$;

R$^6$ is hydrogen, C$_{1-6}$alkyl, —(CR$^{20}$R$^{21}$)$_p$—C$_{3-10}$cycloalkyl, cyanoC$_{1-6}$alkyl, —C$_{1-6}$alkylCO$_2$R$^{24}$, aminocarbonylC$_{1-6}$alkyl, —C$_{1-6}$alkyl-NR$^{22}$R$^{23}$, R$^{24}$SO$_2$, R$^{24}$SO$_2$C$_{1-6}$alkyl, —C$_{1-6}$alkyl-OR$^{24}$, —C$_{1-6}$alkyl-SR$^{24}$, —C$_{1-6}$alkylCONR$^{22}$—C$_{1-6}$alkyl-NR$^{22}$R$^{23}$, —C$_{1-6}$alkylCONR$^{22}$—C$_{1-6}$alkyl-Het$^2$, —C$_{1-6}$alkyl CONR$^{22}$—C$_{1-6}$alkyl-Ar$^2$, —C$_{1-6}$alkyl CONR$^{22}$-Het$^2$, —C$_{1-6}$alkyl CONR$^{22}$Ar$^2$, —C$_{1-6}$alkyl CONR$^{22}$—O—C$_{1-6}$alkyl, —C$_{1-6}$alkyl CONR$^{22}$—C$_{1-6}$alkenyl, -Alk-Ar$^2$ or -Alk-Het$^2$;

R$^7$ is oxygen or sulphur; or R$^6$ and R$^7$ together form a trivalent radical of formula:

| | | | |
|---|---|---|---|
| —CR$^{30}$=CR$^{31}$—N= | (x-1), | —CR$^{30}$=CR$^{31}$—CR$^{32}$= | (x-6), |
| —CR$^{30}$=N—N= | (x-2), | —CR$^{30}$=N—CR$^{31}$= | (x-7), |
| —C(=O)—NH—N= | (x-3), | —C(=O)—NH—CR$^{30}$= | (x-8), |
| —N=N—N= | (x-4), | —N=N—CR$^{30}$= | (x-9), or |
| —N=CR$^{30}$—N= | (x-5), | —CH$_2$—(CH$_2$)$_{0-1}$—CH$_2$—N= | (x-10), | wherein each R$^{30}$, R$^{31}$ and R$^{32}$ are independently hydrogen, C$_{1-6}$ alkyl, —OR$^{24}$, —COOR$^{24}$, —NR$^{22}$R$^{23}$, —C$_{1-6}$ alkylOR$^{24}$, —C$_{1-6}$ alkylSR$^{24}$, R$^{23}$R$^{22}$NC$_{1-6}$alkyl-, —CONR$^{22}$R$^{23}$, C$_{2-6}$alkenyl, C$_{2-6}$alkenylAr$^2$, C$_{2-6}$alkenylHet$^2$, cyano, amino, thio, C$_{1-6}$ alkylthio, —O-Ar$^2$, —S—Ar$^2$ or Ar$^2$;

Ar$^2$ is phenyl, naphthyl or phenyl or naphthyl substituted by one to five substituents each independently selected from halo, hydroxy, cyano, nitro, C$_{1-6}$alkyl, haloC$_{1-6}$alkyl, -alkylNR$^{22}$R$^{23}$, C$_{1-6}$alkyloxy, OCF$_3$, hydroxycarbonyl, C$_{1-6}$alkyloxycarbonyl, aryloxy, —NR$^{22}$R$^{23}$, C$_{1-6}$alkylsulfonylamino, oxime or phenyl, or a bivalent substituent of formula —O—CH$_2$—O— or —O—CH$_2$—CH$_2$—O—;

Het$^2$ is a mono- or bi-cyclic heterocyclic ring containing one or more heteroatoms selected from oxygen, sulphur and nitrogen, and optionally substituted by one or two substituents each independently selected from halo, hydroxy, cyano, nitro, C$_{1-6}$alkyl, haloC$_{1-6}$alkyl, -alkylNR$^{22}$R$^{23}$, C$_{1-6}$alkyloxy, OCF$_3$, hydroxycarbonyl, C$_{1-6}$alkyloxycarbonyl, —CONR$^{22}$R$^{23}$, —NR$^{22}$R$^{23}$, C$_{1-6}$alkylsulfonylamino, oxime or phenyl.

2. A compound according to claim 1 in which:

r and s are each independently 0, 1 or 2;

t is 0 or 1;

>Y$^1$—Y$^2$— is a trivalent radical of formula

>C=N—    (y-1)

>C=CR$^9$—    (y-2)

wherein R$^9$ is hydrogen, cyano, halo, C$_{1-6}$alkyl, hydroxyC$_{1-6}$alkyl, hydroxycarbonyl or aminocarbonyl;

Z is C$_{1-2}$ alkanediyl;

R$^1$ is halo, C$_{1-6}$alkyl, —(CR$^{20}$R$^{21}$)$_p$—C$_{3-10}$cycloalkyl, trihalomethyl, trihalomethoxy, C$_{2-6}$alkenyl, hydroxycarbonylC$_{2-6}$alkenyl, C$_{2-6}$alkynyl, C$_{1-6}$alkyloxy, hydroxyC$_{1-6}$alkyloxy, aminoC$_{1-6}$alkyloxy, C$_{1-6}$alkylthio, hydroxycarbonyl, C$_{1-6}$alkyloxycarbonyl, —CONR$^{22}$R$^{23}$ or —CH=NOR$^{25}$; or two R$^1$ substituents adjacent to one another on the phenyl ring may independently form together a bivalent radical of formula —O—CH$_2$—O—    (a-1)

—O—CH$_2$—CH$_2$—O—    (a-2)

R$^2$ is halo, cyano, nitro, C$_{1-6}$alkyl, cyanoC$_{1-6}$alkyl, —C$_{1-6}$alkyl NR$^{22}$R$^{23}$; cyanoC$_{2-6}$alkenyl, —NR$^{22}$R$^{23}$, —CHO, —CR$^{24}$=N—OR$^{25}$, C$_{1-6}$alkyloxycarbonyl or —CONR$^{22}$R$^{23}$; or two R$^2$ substituents adjacent to one another on the phenyl ring may independently form together a bivalent radical of formula —O—CH$_2$—O—    (a-1)

—O—CH$_2$—CH$_2$—O—    (a-2)

R$^3$ is hydrogen, C$_{1-6}$alkyl, —(CR$^{20}$R$^{21}$)$_p$—C$_{3-10}$cycloalkyl, haloC$_{1-6}$alkyl, cyanoC$_{1-6}$alkyl, hydroxyC$_{1-6}$alkyl, C$_{1-6}$alkyloxyC$_{1-6}$alkyl, —C$_{1-6}$alkyl NR$^{22}$R$^{23}$, Het$^2$C$_{1-6}$alkyl, —C$_{2-6}$alkenylNR$^{22}$R$^{23}$, or -Het$^2$, or a group of formula —O—R$^{10}$    (b-1)

—NR$^{11}$R$^{12}$    (b-3), wherein

R$^{10}$ is hydrogen, C$_{1-6}$alkyl, or —(CR$^{20}$R$^{21}$)$_p$—C$_{3-10}$cycloalkyl, or a group of formula -Alk-OR$^{13}$ or -Alk-NR$^{14}$R$^{15}$;

R$^{11}$ is hydrogen or C$_{1-6}$alkyl;

$R^{12}$ is hydrogen, hydroxy, $C_{1-6}$alkyl, $-(CR^{20}R^{21})_p-C_{3-10}$cycloalkyl, $C_{1-6}$alkyloxy, $C_{1-6}$alkylcarbonyl, aryl$C_{1-6}$alkylcarbonyl, Het$^2$$C_6$alkylcarbonyl, aminocarbonyl, or a radical of formula -Alk-OR$^{13}$ or Alk-NR$^{14}$R$^{15}$;

wherein Alk is $C_{1-6}$alkanediyl;

$R^{13}$ is hydrogen, $C_{1-6}$alkyl or $-(CR^{20}R^{21})_p-C_{3-10}$cycloalkyl;

$R^{14}$ is hydrogen, $C_{1-6}$alkyl, or $-(CR^{20}R^{21})_p-C_{3-10}$cycloalkyl;

$R^{15}$ is hydrogen or $C_{1-6}$alkyl;

$R^4$ is a radical of formula (c-2) or (c-3) wherein $R^{16}$ is hydrogen, halo or $C_{1-6}$alkyl, $R^{17}$ is hydrogen, $C_{1-6}$alkyl, $-(CR^{20}R^{21})_p-C_{3-10}$cycloalkyl, $C_{1-6}$alkyloxy$C_{1-6}$alkyl or trifluoromethyl;

$R^{18}$ is hydrogen, $C_{1-6}$alkyl or $-(CR^{20}R^{21})_p-C_{3-10}$cycloalkyl; and $R^{18a}$ is hydrogen;

$R^5$ is cyano, halo, $C_{1-6}$alkyl, $C_{2-6}$alkynyl, $C_{1-6}$alkyloxy or $C_{1-6}$alkyloxycarbonyl;

$R^6$ is hydrogen, $C_{1-6}$alkyl, $-C_{1-6}$alkyl$CO_2R^{24}$, $-C_{1-6}$alkylC(O)NR$^{22}$R$^{23}$, -Alk-Ar$^2$, -AlkHet$^2$ or $-(CR^{20}R^{21})_p-C_{3-10}$cycloalkyl;

$R^7$ is oxygen or sulphur; or $R^6$ and $R^7$ together form a trivalent radical of formula (x-1), (x-2), (x-3), (x-4) or (x-9); and Het$^2$ is a 5- or 6-membered monocyclic heterocyclic ring containing one, two or three heteroatoms selected from oxygen, sulphur or nitrogen for example pyrrolidinyl, imidazolyl, triazolyl, pyridyl, pyrimidinyl, furyl, morpholinyl, piperazinyl, piperidinyl, thiophenyl, thiazolyl or oxazolyl, or a 9- or 10-membered bicyclic heterocyclic ring especially one in which a benzene ring is fused to a heterocyclic ring containing one, two or three heteroatoms selected from oxygen, sulphur or nitrogen for example indolyl, quinolinyl, benzimidazolyl, benzotriazolyl, benzoxazolyl, benzothiazolyl or benzodioxolanyl.

3. A compound according to claim 1 in which:

r is 0, 1 or 2;

s is 0 or 1;

t is 0;

$>Y^1-Y^2-$ is a trivalent radical of formula (y-1) or (y-2), wherein $R^9$ is hydrogen or halo;

Z is $C_{1-2}$ alkanediyl;

$R^1$ is halo, $C_{1-6}$alkyl, $C_{2-6}$alkenyl, $C_{2-6}$alkynyl, or two $R^1$ substituents ortho to one another on the phenyl ring may independently form together a bivalent radical of formula (a-1);

$R^2$ is halo, cyano, nitro, $-CHO$, $-CR^{24}=N-OR^{25}$ (wherein $R^{24}$ is hydrogen and $R^{25}$ is hydrogen or $C_{1-6}$alkyl), or two $R^2$ substituents ortho to one another on the phenyl ring may independently form together a bivalent radical of formula (a-1);

$R^3$ is hydrogen or a group of formula (b-1) or (b-3) wherein $R^{10}$ is hydrogen or a group of formula -Alk-OR$^{13}$; $R^{11}$ is hydrogen;

$R^{12}$ is hydrogen, $C_{1-6}$alkyl, $C_{1-6}$alkylcarbonyl, hydroxy or $C_{1-6}$alkyloxy;

Alk is $C_{1-6}$alkanediyl and $R^{13}$ is hydrogen;

$R^4$ is a group of formula (c-2) or (c-3) wherein $R^{16}$ is hydrogen, halo or $C_{1-6}$alkyl;

$R^{17}$ is hydrogen or $C_{1-6}$alkyl;

$R^{18}$ is hydrogen or $C_{1-6}$alkyl; and $R^{18a}$ is hydrogen;

$R^6$ is hydrogen, $-(CR^{20}R^{21})_p-C_{3-10}$cycloalkyl, $-C_{1-6}$alkyl$CO_2R^{24}$, $-C_{1-6}$alkylC(O)NR$^{22}$R$^{23}$, -Alk-Ar$^2$ or -AlkHet$^2$ or $C_{1-6}$alkyl;

$R^7$ is oxygen or sulphur; or $R^6$ and $R^7$ together form a trivalent radical of formula (x-1), (x-2), (x-3), (x-4) or (x-9); and aryl is phenyl.

4. A compound according to claim 1 in which:

r is 0 or 1, s is 1, t is 0, $>Y^1-Y^2$ is a trivalent radical of formula (y-1) or (y-2), Z is $C_{1-2}$alkanediyl, $R^1$ is halo, $C_{1-6}$alkyl or forms a bivalent radical of formula (a-1), $R^2$ is halo or cyano, $R^3$ is hydrogen or a radical of formula (b-1) or (b-3) (wherein $R^{10}$ is hydrogen or -Alk-OR$^{13}$, $R^{11}$ is hydrogen, $R^{12}$ is hydrogen or $C_{1-6}$alkylcarbonyl, and $R^{13}$ is hydrogen);

$R^4$ is a radical of formula (c-2) or (c-3) (wherein $R^{16}$ is hydrogen, $R^{17}$ is $C_{1-6}$alkyl, $R^{18}$ is $C_{1-6}$alkyl and $R^{18a}$ is hydrogen);

$R^6$ is hydrogen, $C_{1-6}$alkyl, $-CH_2-C_{3-10}$cycloalkyl, $-C^{1-6}$alkyl$CO_2R^{24}$ ($R^{24}$=H or Et), aminocarbonyl$C_{1-6}$alkyl, -Alk-Ar$^2$ or -AlkHet$^2$; and $R^7$ is oxygen or sulphur; or $R^6$ and $R^7$ together form a trivalent radical of formula (x-2), (x-3) or (x-4).

5. A compound according claim 1 in which:

r is 0 or 1, s is 1, t is 0, $>Y^1-Y^2$ is a trivalent radical of formula (y-1) or (y-2), Z is $C_{1-2}$ alkanediyl, $R^1$ is halo, $R^2$ is halo or cyano, $R^3$ is hydrogen or a radical of formula (b-1) or (b-3) (wherein $R^9$ is hydrogen, $R^{10}$ is hydrogen, $R^{11}$ is hydrogen and $R^{12}$ is hydrogen or $C_{1-6}$alkylcarbonyl;

$R^4$ is a radical of formula (c-2) or (c-3) (wherein $R^{16}$ is hydrogen, $R^{17}$ is $C_{1-6}$alkyl, $R^{18}$ is $C_{1-6}$alkyl and $R^{18a}$ is hydrogen);

$R^6$ is hydrogen, $C_{1-6}$alkyl, $-CH_2-C_{3-10}$cycloalkyl or $-C_{1-6}$alkylAr$^2$; and $R^7$ is oxygen or sulphur; or $R^6$ and $R^7$ together form a trivalent radical of formula (x-2) or (x-4).

6. A compound according claim 1 in which:

r and s are 1, t is 0, $>Y^1-Y^2$ is a trivalent radical of formula (y-1) or (y-2), Z is $-(CH_2)_2-$, $R^1$ is 3-chloro, $R^2$ is 4-chloro or 4-cyano, $R^3$ is a radical of formula (b-1) or (b-3) (wherein $R^9$ is hydrogen, $R^{10}$ and $R^{11}$ are hydrogen, and $R^{12}$ is hydrogen or $C_{1-6}$alkylcarbonyl);

$R^4$ is a radical of formula (c-2) or (c-3) (wherein $R^{16}$ is hydrogen, $R^{17}$ is $C_{1-6}$alkyl, $R^{18}$ is $C_{1-6}$alkyl, and $R^{18a}$ is hydrogen);

$R^6$ is hydrogen, $C_{1-6}$alkyl, $-CH_2-C_{3-10}$cycloalkyl or $-C_{1-6}$alkylAr$^2$; and $R^7$ is oxygen or sulphur; or $R^6$ and $R^7$ together form a trivalent radical of formula (x-4).

7. A compound selected from:

6-[amino(4-chlorophenyl)(1-methyl-1H-imidazol-5-yl)methyl]-4-[2-(3-chlorophenyl)ethyl]-1-methyl-2(1H)-quinolinone;

4-[2-(3-chlorophenyl)ethyl]-6-[(4-chlorophenyl)hydroxy(1-methyl-1H-imidazol-5-yl)methyl]-1-methyl-2(1H)-quinolinone;

α-(4-chlorophenyl)-5-[2-(3-chlorophenyl)ethyl]-α-(1-methyl-1H-imidazol-5-yl)-tetrazolo[1,5-α]quinoline-7-methanamine;

N-[(4-chlorophenyl)[5-[2-(3-chlorophenyl)ethyl]tetrazolo[1,5-α]quinolin-7-yl](1-methyl-1H-imidazol-5-yl)methyl]-acetamide;

N-[(4-chlorophenyl)(1-methyl-1H-imidazol-5-yl)[5-(2-phenylethyl)tetrazolo[1,5-α]quinolin-7-yl]methyl]-acetamide; and 4-[2-(3-chlorophenyl)ethyl]-6-[(4-chlorophenyl)hydroxy(4-methyl-4H-1,2,4-triazol-3-yl)methyl]-1-methyl-2(1H)-quinolinone;

and their pharmaceutically acceptable salts.

8. A process for the preparation of a compound as claimed in claim 1 which comprises:

a) cyclising a compound of formula (II):

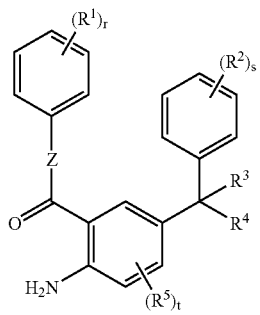

with a reagent serving to form a compound of formula (I) in which $R^6$ is hydrogen and $R^7$ is oxygen;

b) reacting a compound of formula (III):

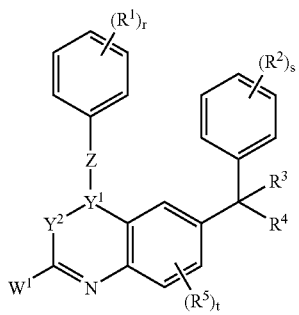

in which $W^1$ represents a replaceable or reactive group, with a reagent serving either to react with or replace the $W^1$ group in compound (III) to form a compound of formula (I) in which $R^6$ is hydrogen and $R^7$ is an oxygen or sulphur group or to react with the $W^1$ group and the adjacent nitrogen atom to form directly or indirectly a compound of formula (I) in which $R^6$ and $R^7$ together form a trivalent radical selected from formulae (x-1) to (x-10); or c) reacting a compound of formula (IV):

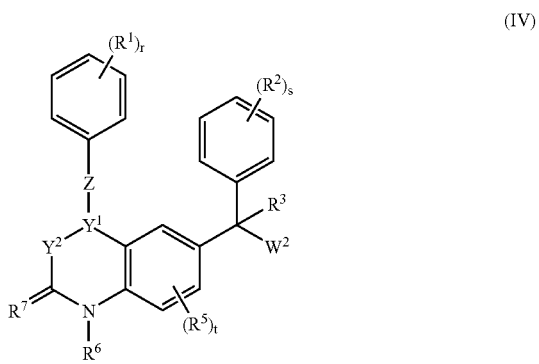

in which $W^2$ is a replaceable group, with an imidazole reagent serving to replace the group $W^2$ with an $R^4$ group of formula (c-1); or d) reacting a compound of formula (V):

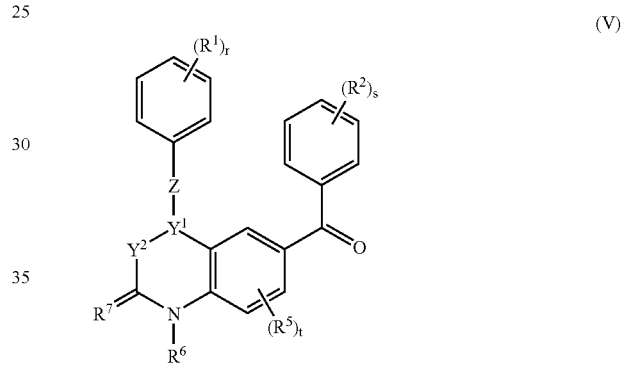

with an imidazole reagent to form a compound of formula (I) in which $R^4$ is a group of formula (c-2), or with a 3-mercapto-4-$C_{1-6}$alkyl-1,2,4-triazole reagent to form the corresponding 3-mercapto-4-$C_{1-6}$alkyl-1,2,4-triazole derivative, which is optionally methylated to form the corresponding 3-methylmercapto derivative, and subsequently removing the 3-mercapto or 3-methylmercapto group to form a compound of formula (I) in which $R^4$ is a group of formula (c-3) in which $R^{18}$ is a $C_{1-6}$alkyl group;

or with a 3-bromopyridyl reagent to form a compound of formula (I) wherein $R^4$ is a group of formula (c-4); or e) reacting a compound of formula (VI):

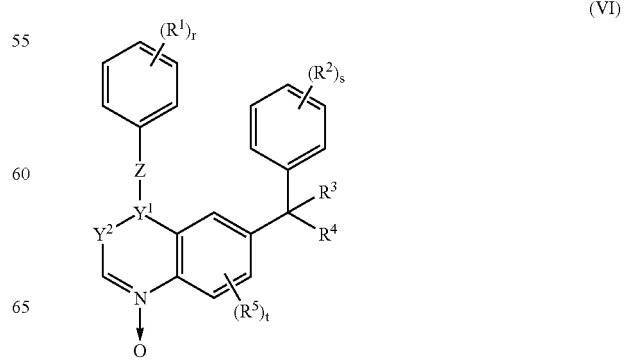

with a reagent serving to convert the said compound (VI) to a compound of formula (I) in which $R^6$ is hydrogen and $R^7$ is oxygen;

and optionally effecting one or more of the following conversions in any desired order:
- (i) converting a compound of formula (I) into a different compound of formula (I);
- (ii) converting a compound of formula (I) into a pharmaceutically acceptable salt or N-oxide thereof;
- (iii) converting a pharmaceutically acceptable salt or N-oxide of a compound of formula (I) into the parent compound of formula (I); and
- (iv) preparing a stereochemical isomeric form of a compound of formula (I) or a pharmaceutically acceptable salt or N-oxide thereof.

9. A pharmaceutical composition comprising a pharmaceutically acceptable carrier, and an active ingredient comprising a therapeutically effective amount of a compound of claim 1.

10. A pharmaceutical composition comprising a pharmaceutically acceptable carrier, and an active ingredient comprising a therapeutically effective amount of a compound of claim 2.

11. A pharmaceutical composition comprising a pharmaceutically acceptable carrier, and an active ingredient comprising a therapeutically effective amount of a compound of claim 3.

12. A pharmaceutical composition comprising a pharmaceutically acceptable carrier, and an active ingredient comprising a therapeutically effective amount of a compound of claim 4.

13. A pharmaceutical composition comprising a pharmaceutically acceptable carrier, and an active ingredient comprising a therapeutically effective amount of a compound of claim 5.

14. A pharmaceutical composition comprising a pharmaceutically acceptable carrier, and an active ingredient comprising a therapeutically effective amount of a compound of claim 6.

15. A pharmaceutical composition comprising a pharmaceutically acceptable carrier, and an active ingredient comprising a therapeutically effective amount of a compound of claim 7.

* * * * *